United States Patent
Gachotte et al.

(10) Patent No.: US 10,370,674 B2
(45) Date of Patent: *Aug. 6, 2019

(54) GENERATION OF TRANSGENIC CANOLA WITH LOW OR NO SATURATED FATTY ACIDS

(71) Applicant: Dow AgroSciences LLC, Indianapolis, IN (US)

(72) Inventors: Daniel J. Gachotte, Indianapolis, IN (US); Ann Owens Merlo, Carmel, IN (US); Mark A. Thompson, Zionsville, IN (US); Terence A. Walsh, Carmel, IN (US); Beth Rubin Wilson, Indianapolis, IN (US); Mary Welter, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 97 days.

This patent is subject to a terminal disclaimer.

(21) Appl. No.: 15/398,481

(22) Filed: Jan. 4, 2017

(65) Prior Publication Data

US 2017/0112160 A1    Apr. 27, 2017

Related U.S. Application Data

(63) Continuation of application No. 14/578,008, filed on Dec. 19, 2014, now Pat. No. 9,617,555, which is a continuation-in-part of application No. 13/168,742, filed on Jun. 24, 2011, which is a continuation-in-part of application No. 11/576,750, filed as application No. PCT/US2005/036052 on Oct. 7, 2005, now abandoned.

(60) Provisional application No. 60/617,532, filed on Oct. 8, 2004.

(51) Int. Cl.
*C12N 15/82* (2006.01)
*C12N 5/14* (2006.01)
*C12N 9/02* (2006.01)

(52) U.S. Cl.
CPC ....... *C12N 15/8247* (2013.01); *C12N 9/0083* (2013.01); *C12Y 114/00* (2013.01); *C12Y 114/99* (2013.01); *C12N 5/14* (2013.01); *C12Y 114/19001* (2013.01)

(58) Field of Classification Search
None
See application file for complete search history.

(56) References Cited

U.S. PATENT DOCUMENTS

| | | |
|---|---|---|
| 5,777,201 A | 7/1998 | Poutre et al. |
| 6,495,738 B1 | 12/2002 | Folkerts et al. |
| 6,825,335 B1 | 11/2004 | Martin et al. |
| 9,617,555 B2 * | 4/2017 | Gachotte .............. C12N 9/0083 |
| 2006/0080750 A1 | 4/2006 | Fillatti et al. |
| 2008/0092254 A1 | 4/2008 | Shah et al. |
| 2011/0302672 A1 | 12/2011 | Merlo et al. |

OTHER PUBLICATIONS

Gelvin 2003 (Microbiology and Molecular Biology Reviews Mar.: p. 16-37).
International Search Report and Written Opinion for PCT/US2014/071705, dated Jul. 29, 2015.

* cited by examiner

*Primary Examiner* — Matthew R Keogh

(57) ABSTRACT

Compositions and methods include genetically encoding and expressing a novel delta-9 desaturase in plant cells. In some embodiments, methods of expressing nucleic acids in a plant cell to take advantage of the delta-9 desaturase enzyme's activity, such that the percent composition of saturated fatty acids in plant seeds is decreased and there is a concomitant increase in $\Delta 9$ fatty acids. In other embodiments, amino acid sequences have delta-9 desaturase activity. Methods can involve expression of delta-9 desaturase in plant cells, plant materials, and whole plants for the purpose of increasing the amount of mono unsaturated fatty acids in whole plants, plant seeds, and plant materials, for example, seeds.

3 Claims, 5 Drawing Sheets
Specification includes a Sequence Listing.

SEQUENCE LISTING

<160> NUMBER OF SEQ ID NOS: 33

<210> SEQ ID NO 1
<211> LENGTH: 455
<212> TYPE: PRT
<213> ORGANISM: Aspergillus nidulans

<400> SEQUENCE: 1

Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
            20                  25                  30

His Val Asn Trp Leu Asn Val Phe Leu Ile Ile Gly Ile Pro Leu Tyr
        35                  40                  45

Gly Cys Ile Gln Ala Phe Trp Val Pro Leu Gln Leu Lys Thr Ala Ile
    50                  55                  60

Trp Ala Val Ile Tyr Tyr Phe Phe Thr Gly Leu Gly Ile Thr Ala Gly
65                  70                  75                  80

Tyr His Arg Leu Trp Ala His Cys Ser Tyr Ser Ala Thr Leu Pro Leu
                85                  90                  95

Arg Ile Trp Leu Ala Ala Val Gly Gly Gly Ala Val Glu Gly Ser Ile
            100                 105                 110

Arg Trp Trp Ala Arg Asp His Arg Ala His His Arg Tyr Thr Asp Thr
        115                 120                 125

Asp Lys Asp Pro Tyr Ser Val Arg Lys Gly Leu Leu Tyr Ser His Leu
    130                 135                 140

Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
                165                 170                 175

Tyr Leu Lys Val Val Phe Thr Met Gly Leu Ala Val Pro Met Leu Val
            180                 185                 190

Ala Gly Leu Gly Trp Gly Asp Trp Leu Gly Gly Phe Val Tyr Ala Gly
        195                 200                 205

Ile Leu Arg Ile Phe Phe Val Gln Gln Ala Thr Phe Cys Val Asn Ser
    210                 215                 220

Leu Ala His Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
            245                 250                 255

Asn Phe His His Glu Phe Pro Ser Asp Tyr Arg Asn Ala Ile Glu Trp
        260                 265                 270

His Gln Tyr Asp Pro Thr Lys Trp Ser Ile Trp Ala Trp Lys Gln Leu
    275                 280                 285

Gly Leu Ala Tyr Asp Leu Lys Lys Phe Arg Ala Asn Glu Ile Glu Lys
290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
                325                 330                 335

Asp Tyr Val Glu Gln Ala Lys Asn Gly Arg Gly Leu Val Ala Ile Ala
            340                 345                 350

Gly Val Val His Asp Val Thr Asp Phe Ile Lys Asp His Pro Gly Gly
        355                 360                 365

Lys Ala Met Ile Ser Ser Gly Ile Gly Lys Asp Ala Thr Ala Met Phe
370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Gly Cys Glu Val Glu Ile Trp
                405                 410                 415

Lys Arg Ala Gln Lys Glu Asn Val Glu Tyr Val Arg Asp Gly Ser Gly
            420                 425                 430

Gln Arg Val Ile Arg Ala Gly Glu Gln Pro Thr Lys Ile Pro Glu Pro
        435                 440                 445

Ile Pro Thr Ala Asp Ala Ala
    450                 455

<210> SEQ ID NO 2
<211> LENGTH: 1368
<212> TYPE: DNA
<213> ORGANISM: Artificial Sequence
<220> FEATURE:
<223> OTHER INFORMATION: Synthesized nucleodtide encoding Aspergillus
      nidulas Delta 9 desaturase v3

<400> SEQUENCE: 2
atgtctgctc caaccgctga catcagggct agggctccag aggctaagaa ggttcacatc      60
gctgataccg ctatcaacag gcacaattgg tacaagcacg tgaactggct caacgtcttc     120
ctcatcatcg gaatcccact ctacggatgc atccaagctt tctgggttcc acttcaactc     180
aagaccgcta tctgggctgt gatctactac ttcttcaccg gacttggaat caccgctgga     240
taccacaggc tttgggctca ctgctctata tctgctactc ttccacttag gatctggctt     300
gctgctgttg gaggaggagc tgttgaggga tctatcagat ggtgggctag ggatcacagg     360
gctcatcata ggtacaccga taccgacaag gacccatact ctgttaggaa gggacttctc     420
tactctcacc ttggatggat ggtgatgaag cagaacccaa agaggatcgg aaggaccgac     480
atctctgatc tcaacgagga cccagttgtt gtttggcaac acaggaacta cctcaaggtt     540
gtgttcacca tgggacttgc tgttccaatg cttgttgctg acttggatg gggagattgg     600 cttggaggat tcgtgtacgc tggaatcctt aggatcttct tcgttcaaca agctaccttc     660
tgcgtgaact ctcttgctca ctggcttgga atcaaccat tcgatgatag gaactctcct     720

| | | | | |
|---|---|---|---|---|
| agggatcacg | tgatcaccgc | tcttgttacc | cttggagagg | gataccacaa cttccaccac | 780 |
| gagttcccat | ctgactacag | gaacgctatc | gagtggcacc | agtacgatcc taccaagtgg | 840 |
| tctatctggg | cttggaagca | acttggattg | gcttacgatc | tcaagaagtt cagggctaac | 900 |
| gagatcgaga | agggaagggt | tcaacaactt | cagaagaagc | ttgataggaa gagggctact | 960 |
| cttgattggg | gaaccccact | tgatcaactt | ccagtgatgg | aatgggatga ctacgttgag | 1020 |
| caagctaaga | acgaaggggg | acttgttgct | atcgctggag | ttgttcacga tgttaccgac | 1080 |
| ttcatcaagg | atcacccagg | aggaaaggct | atgatctctt | ctggaatcgg aaaggatgct | 1140 |
| accgctatgt | tcaacggagg | agtgtactac | cactctaacg | cagctcacaa ccttcttagc | 1200 |
| accatgaggg | tgggagtgat | caggggagga | tgcgaggttg | agatctggaa gagggctcag | 1260 |
| aaggagaacg | ttgagtacgt | tagggatgga | tctggacaaa | gggtgatcag ggctggagag | 1320 |
| caaccaacca | agatcccaga | gccaatccca | accgctgatg | ctgcttga | 1368 |

<210> SEQ ID NO 3
<211> LENGTH: 2912
<212> TYPE: DNA
<213> ORGANISM: Artificial Sequence
<220> FEATURE:
<223> OTHER INFORMATION: The first plant transcription unit comprising
      Aspergillus nidulans delta 9 desaturase v3

<400> SEQUENCE: 3

| | | | | |
|---|---|---|---|---|
| ctcccagtat | cattatagtg | aaagttttgg | ctctctcgcc | ggtggttttt tacctctatt | 60 |
| taaaggggtt | ttccacctaa | aaattctggt | atcattctca | ctttacttgt tactttaatt | 120 |
| tctcataatc | tttggttgaa | attatcacgc | ttccgcacac | gatatcccta caaatttatt | 180 |
| atttgttaaa | cattttcaaa | ccgcataaaa | ttttatgaag | tcccgtctat ctttaatgta | 240 |
| gtctaacatt | ttcatattga | aatatataat | ttacttaatt | ttagcgttgg tagaaagcat | 300 |
| aatgatttat | tcttattctt | cttcatataa | atgtttaata | tacaatataa acaaattctt | 360 |
| taccttaaga | aggatttccc | attttatatt | ttaaaaatat | atttatcaaa tatttttcaa | 420 |
| ccacgtaaat | ctcataataa | taagttgttt | caaaagtaat | aaaatttaac tccataattt | 480 |
| ttttattcga | ctgatcttaa | agcaacaccc | agtgacacaa | ctagccattt ttttctttga | 540 |
| ataaaaaaat | ccaattatca | ttgtattttt | tttatacaat | gaaaatttca ccaaacaatg | 600 |
| atttgtggta | tttctgaagc | aagtcatgtt | atgcaaaatt | ctataattcc catttgacac | 660 |
| tacgaagta | actgaagatc | tgcttttaca | tgcgagacac | atcttctaaa gtaattttaa | 720 |
| taatagttac | tatattcaag | atttcatata | tcaaatactc | aatattactt ctaaaaaatt | 780 |
| aattagatat | aattaaaata | ttactttttt | aattttaagt | ttaattgttg aatttgtgac | 840 |
| tattgattta | ttattctact | atgtttaaat | tgttttatag | atagtttaaa gtaaatataa | 900 |
| gtaatgtagt | agagtgttag | agtgttaccc | taaaccataa | actataagat ttatggtgga | 960 |
| ctaattttca | tatatttctt | attgcttta | cctttcttg | gtatgtaagt ccgtaactgg | 1020 |
| aattactgtg | ggttgccatg | acactctgtg | gtcttttggt | tcatgcatgg atgcttgcgc | 1080 |
| aagaaaaaga | caaagaacaa | agaaaaaaga | caaaacagag | agacaaaacg caatcacaca | 1140 |
| accaactcaa | attagtcact | ggctgatcaa | gatcgccgcg | tccatgtatg tctaaatgcc | 1200 |
| atgcaaagca | acacgtgctt | aacatgcact | ttaaatggct | cacccatctc aacccacaca | 1260 |
| caaacacatt | gcctttttct | tcatcatcac | cacaaccacc | tgtatatatt cattctcttc | 1320 |
| cgccacctca | atttcttcac | ttcaacacac | gtcaacctgc | atatgcgtgt catcccatgc | 1380 |

```
ccaaatctcc atgcatgttc caaccacctt ctctcttata taatacctat aaatacctct    1440
aatatcactc acttctttca tcatccatcc atccagagta ctactactct actactataa    1500
taccccaacc caactcatat tcaatactac tctaggatcc aacaatgtct gctccaaccg    1560
ctgacatcag ggctagggct ccagaggcta agaaggttca catcgctgat accgctatca    1620
acaggcacaa ttggtacaag cacgtgaact ggctcaacgt cttcctcatc atcggaatcc    1680
cactctacgg atgcatccaa gctttctggg ttccacttca actcaagacc gctatctggg    1740
ctgtgatcta ctacttcttc accggacttg gaatcaccgc tggataccac aggctttggg    1800
ctcactgctc atactctgct actcttccac ttaggatctg gcttgctgct gttggaggag    1860
gagctgttga gggatctatc agatggtggg ctagggatca cagggctcat cataggtaca    1920
ccgataccga caaggaccca tactctgtta ggaagggact tctctactct cacccttggat   1980
```

```
tgaaagcaac gcaccacaaa acgaagaccc ctttacaaat acatctcatc ccttagtacc      540
ctcttactac tgtcccgaca caaactcaaa acaaggtacc ctgcagggat ccaacaatgt      600
ctgctccaac cgctgacatc agggctaggg ctccagaggc taagaaggtt cacatcgctg      660
ataccgctat caacaggcac aattggtaca agcacgtgaa ctggctcaac gtcttcctca      720
tcatcggaat cccactctac ggatgcatcc aagctttctg gttccactt caactcaaga       780 ccgctatctg gctgtgatc tactacttct tcaccggact tggaatcacc gctggatacc       840
acaggctttg ggctcactgc tcatactctg ctactcttcc acttaggatc tggcttgctg      900
ctgttggagg aggagctgtt gagggatcta tcagatggtg ggctagggat cacagggctc      960
atcataggta caccgatacc gacaaggacc catactctgt taggaaggga cttctctact     1020
ctcaccttgg atggatggtg atgaagcaga acccaaagag gatcggaagg accgacatct     1080
ctgatctcaa cgaggaccca gttgttgttt ggcaacacag gaactacctc aaggttgtgt     1140
tcaccatggg acttgctgtt ccaatgcttg ttgctggact tggatgggga gattggcttg     1200
gaggattcgt gtacgctgga atccttagga tcttcttcgt tcaacaagct accttctgcg     1260
tgaactctct tgctcactgg cttggagatc aaccattcga tgataggaac tctcctaggg     1320
atcacgtgat caccgctctt gttacccttg agagggata ccacaacttc caccacgagt      1380
tcccatctga ctacaggaac gctatcgagt ggcaccagta cgatcctacc aagtggtcta     1440
tctgggcttg gaagcaactt ggattggctt acgatctcaa gaagttcagg gctaacgaga     1500
tcgagaaggg aaggggttcaa caacttcaga agaagcttga taggaagagg gctactcttg     1560
attggggaac cccacttgat caacttccag tgatggaatg ggatgactac gttgagcaag     1620
ctaagaacgg aagggggactt gttgctatcg ctggagttgt tcacgatgtt accgacttca     1680
tcaaggatca cccaggagga aaggctatga tctcttctgg aatcggaaag gatgctaccg     1740
ctatgttcaa cggaggagtg tactaccact ctaacgcagc tcacaaccct cttagcacca     1800
tgagggtggg agtgatcagg ggaggatgcg aggttgagat ctggaagagg gctcagaagg     1860
agaacgttga gtacgttagg gatggatctg gacaaagggt gatcagggct ggagagcaac     1920
caaccaagat cccagagcca atcccaaccg ctgatgctgc ttgagtagtt agcttaatca     1980
cctaggtcac cagcataatt tttattaatg tactaaatta ctgttttgtt aaatgcaatt     2040
ttgctttctc gggattttaa tatcaaaatc tatttagaaa tacacaatat tttgttgcag     2100
gcttgctgga gaatcgatct gctatcataa aaattacaaa aaaattttat ttgcctcaat     2160 tatttttagga ttggtattaa ggacgcttaa attatttgtc gggtcactac gcatcattgt     2220
gattgagaag atcagcgata cgaaatattc gtagtactat cgataattta tttgaaaatt     2280
cataagaaaa gcaaacgtta catgaattga tgaaacaata caaagacaga taaagccacg     2340
cacatttagg atattggccg agattactga atattgagta agatcacgga atttctgaca     2400
ggagcatgtc ttcaattcag cccaaatggc agttgaaata ctcaaaccgc ccatatgca      2460 ggagcggatc attcattgtt tgtttggttg cctttgccaa catgggagtc caaggtt        2517
```

<210> SEQ ID NO 5
<211> LENGTH: 1828
<212> TYPE: DNA
<213> ORGANISM: Artificial Sequence
<220> FEATURE:
<223> OTHER INFORMATION: Plant transcription unit comprising
      phospinothricin acetyl transferase

<400> SEQUENCE: 5

```
cctgcaggga gattttttcaa atcagtgcgc tagacgtgac gtaagtatcc gagtcagttt      60
ttatttttct actaatttgg tcgtttattt cggcgtgtag gacatggcaa ccgggcctga     120
atttcgcggg tattctgttt ctattccaac tttttcttga tccgcagcca ttaacgactt     180
ttgaatagat acgtctaggg tcgaggggggg atccgtcgag ggggtccacc aaaaacgtaa    240
gcgcttacgt acatggtcga gggggtccac caaaaacgta agcgcttacg tacatggtcg    300
agggggtcca ccaaaaacgt aagcgcttac gtacatggtc gagggggtcc accaaaaacg    360
taagcgctta cgtacatggt cgactagagc gtgacgctcg cggtgacgcc atttcgcctt    420
ttcagaaatg gataaatagc cttgcttcct attatatctt cccaaattac caatacatta    480
cactagcatc tgaatttcat aaccaatctc gatacaccaa atcgcagatc tggatcccaa    540
accatgtctc cggagaggag accagttgag attaggccag ctacagcagc tgatatggcc    600
gcggtttgtg atatcgttaa ccattacatt gagacgtcta cagtgaactt taggacagag    660
ccacaaacac cacaagagtg gattgatgat ctagagaggt gcaagatag ataccttgg     720 ttggttgctg aggttgaggg tgttgtggct ggtattgctt acgctgggcc ctggaaggct    780
aggaacgctt acgattggac agttgagagt actgtttacg tgtcacatag gcatcaaagg    840
ttgggcctag gatctacatt gtacacacat ttgcttaagt ctatggaggc gcaaggtttt    900
aagtctgtgg ttgctgttat aggccttcca aacgatccat ctgttaggtt gcatgaggct    960
ttgggataca cagcccgggg tacattgcgc gcagctggat acaagcatgg tggatggcat   1020
gatgttggtt tttggcaaag ggattttgag ttgccagctc ctccaaggcc agttaggcca   1080
gttacccaaa tctgagtagt tagcttaatc acctagagct cgatcggcgg caatagcttc   1140
ttagcgccat cccgggttga tcctatctgt gttgaaatag ttgcggtggg caaggctctc   1200
tttcagaaag acaggcggcc aaaggaaccc aaggtgaggt gggctatggc tctcagttcc   1260
ttgtggaagc gcttggtcta aggtgcagag gtgttagcgg gatgaagcaa aagtgtccga   1320
ttgtaacaag atatgttgat cctacgtaag gatattaaag tatgtattca tcactaatat   1380
aatcagtgta ttccaatatg tactacgatt tccaatgtct ttattgtcgc cgtatgtaat   1440
cggcgtcaca aaataatccc cggtgacttt cttttaatcc aggatgaaat aatatgttat   1500
tataattttt gcgatttggt ccgttatagg aattgaagtg tgcttgaggt cggtcgccac   1560
cactcccatt tcataatttt acatgtattt gaaaaataaa aatttatggt attcaattta   1620
aacacgtata cttgtaaaga atgatatctt gaaagaaata tagtttaaat atttattgat   1680
aaaataacaa gtcaggtatt atagtccaag caaaaacata aatttattga tgcaagttta   1740
aattcagaaa tatttcaata actgattata tcagctggta cattgccgta gatgaaagac   1800
tgagtgcgat attatggtgt aatacata                                     1828
```

<210> SEQ ID NO 6
<211> LENGTH: 29
<212> TYPE: DNA
<213> ORGANISM: Artificial Sequence
<220> FEATURE:
<223> OTHER INFORMATION: Patv5 forward primer

<400> SEQUENCE: 6

```
acaagagtgg attgatgatc tagagaggt                                      29
```

<210> SEQ ID NO 7
<211> LENGTH: 29
<212> TYPE: DNA

```
<213> ORGANISM: Artificial Sequence
<220> FEATURE:
<223> OTHER INFORMATION: patv5 reverse primer

<400> SEQUENCE: 7
ctttgatgcc tatgtgacac gtaaacagt                                          29

<210> SEQ ID NO 8
<211> LENGTH: 29
<212> TYPE: DNA
<213> ORGANISM: Artificial Sequence
<220> FEATURE:
<223> OTHER INFORMATION: pat v5 probe

<400> SEQUENCE: 8
ccagcgtaag caataccagc cacaacacc                                          29

<210> SEQ ID NO 9
<211> LENGTH: 23
<212> TYPE: DNA
<213> ORGANISM: Artificial Sequence
<220> FEATURE:
<223> OTHER INFORMATION: HMG1 forward primer

<400> SEQUENCE: 9
cctctctacc accgtctcac atg                                                23

<210> SEQ ID NO 10
<211> LENGTH: 20
<212> TYPE: DNA
<213> ORGANISM: Artificial Sequence
<220> FEATURE:
<223> OTHER INFORMATION: HMG1 reverse primer

<400> SEQUENCE: 10
gatctggccg gactgtttca                                                    20

<210> SEQ ID NO 11
<211> LENGTH: 25
<212> TYPE: DNA
<213> ORGANISM: Artificial Sequence
<220> FEATURE:
<223> OTHER INFORMATION: HMG1 probe

<400> SEQUENCE: 11
cgctcctcag ctaccacctc aacca                                              25

<210> SEQ ID NO 12
<211> LENGTH: 1523
<212> TYPE: DNA
<213> ORGANISM: Artificial Sequence
<220> FEATURE:
<223> OTHER INFORMATION: PCR amplified fragment of MgD9Ds

<400> SEQUENCE: 12
gaattcatgg cttcgtcatc ttcctccgtg ccggagttgg ctgccgcctt ccctgatggc        60
actaccgact tcaagcccat gaggaacacc aagggctacg acgtcagcaa gccgcacatt       120
tccgagacac ctatgacact caagaactgg cataagcacg tcaactggct caacaccacc       180
ttcatcttgt ttgtgcccct ggctggtctc atatccactt actgggtccc tctgcagtgg       240
aagacggctg tatgggctgt cgtctactac ttcaacaccg gcctgggaat tactgccggt       300
aagtggctct tgaacaaacg agctaggccg ccgcccctgta tccaatcatc tgtatccatc       360
cctagatgct aactagaaaa cttgcgggtt accaccgact ttgggctcac agctcgtaca       420
```

```
aggcctcgct tccgctcaaa atctaccttg ccgccgttgg cgctggtgcc gtcgagggct      480
ccatcagatg gtggtccaac ggtcaccgcg cacaccaccg atacaccgat accgagaagg      540
acccctactc agtccgcaag ggtctcctgt actcacacat gggatggatg cttctgaagc      600
agaaccccaa gaagcagggc cgcaccgaca tcaccgacct gaacgaggac cccgttgtcg      660
tttggcagca ccgcaacttc ctcaagtgtg ttatcttcat ggccctcgtc ttccccacac      720
ttgtggctgg ccttggctgg ggtgactact ggggaggttt catctacgga ggtattctgc      780
gtgtcttctt cgtccagcag gccaccttct gcgtcaactc gcttgcccac tggctcggtg      840
accagccttt cgacgatcgc aactcgccgc gtgatcacgt catcacagcc ctggtcaccc      900
ttggagaggg ataccacaac ttccaccacg agttcccttc ggactaccgc aacgctattg      960
agtggtacca gtatgacccc accaagtggt caatctggat ctggaagcag cttggtcttg     1020
cccacaacct gaagcagttc cgccaaaacg agattgagaa gggacgcgtc cagcagctgc     1080
agaagaagct cgaccagaag cgcgccaagc ttgattgggg tattcccttg gagcagcttc     1140
ccgttgttag ctgggatgac tttgttgagc agtccaagaa cggaaaggct tggattgcag     1200
ttgccggtgt catccacgat gttggtgact catcaaggaa ccaccctggt ggcagagctc     1260
tcatcaactc ggccattggc aaggacgcaa ccgcaatctt caacggcggt gtttacaacc     1320
actccaacgc cgctcacaac ctgctctcga ctatgcgtgt gggtgttttg cgtggcggct     1380
gcgaggttga gatctggaag cgcgcccagt ccgaaaacaa ggacgtctca accgtcgttg     1440
attcttcggg taaccgcatc gtccgcgcgg gtgggcaagc gaccaaggtc gtccagcctg     1500
ttccgggtgc tcaggccgcg tga                                             1523
```

<210> SEQ ID NO 13
<211> LENGTH: 1428
<212> TYPE: DNA
<213> ORGANISM: Artificial Sequence
<220> FEATURE:
<223> OTHER INFORMATION: Intronless MgD9Ds clone

<400> SEQUENCE: 13

```
atggcttcgt catcttcctc cgtgccggag ttggctgccg ccttccctga tggcactacc       60
gacttcaagc ccatgaggaa caccaagggc tacgacgtca gcaagccgca catttccgag      120
acacctatga cactcaagaa ctggcataag cacgtcaact ggctcaacac caccttcatc      180
ttgtttgtgc ccctggctgg tctcatatcc acttactggg tccctctgca gtggaagacg      240
gctgtatggg ctgtcgtcta ctacttcaac accggcctgg gaattactgc cggttaccac      300
cgactttggg ctcacagctc gtacaaggcc tcgcttccgc tcaaaatcta ccttgccgcc      360
gttggcgctg gtgccgtcga gggctccatc agatggtggt ccaacggtca ccgcgcacac      420
caccgataca ccgataccga gaaggacccc tactcagtcc gcaagggtct cctgtactca      480
cacatgggat ggatgcttct gaagcagaac cccaagaagc agggccgcac cgacatcacc      540
gacctgaacg aggaccccgt tgtcgtttgg cagcaccgca acttcctcaa gtgtgttatc      600
ttcatggccc tcgtcttccc cacacttgtg gctggccttg gctggggtga ctactgggga      660
ggtttcatct acgaggtat tctgcgtgtc ttcttcgtcc agcaggccac cttctgcgtc      720
aactcgcttg cccactggct cggtgaccag ccttttcgacg atcgcaactc gccgcgtgat      780
cacgtcatca gcccctggt caccttggga gagggatacc acaacttcca ccacgagttc      840
ccttcggact accgcaacgc tattgagtgg taccagtatg accccaccaa gtggtcaatc      900
```

```
tggatctgga agcagcttgg tcttgcccac aacctgaagc agttccgcca aaacgagatt    960
gagaagggac gcgtccagca gctgcagaag aagctcgacc agaagcgcgc caagcttgat   1020
tggggtattc ccttggagca gcttcccgtt gttagctggg atgactttgt tgagcagtcc   1080
aagaacggaa aggcttggat tgcagttgcc ggtgtcatcc acgatgttgg tgacttcatc   1140
aaggaccacc ctggtggcag agctctcatc aactcggcca ttggcaagga cgcaaccgca   1200
atcttcaacg gcggtgttta caaccactcc aacgccgctc acaacctgct ctcgactatg   1260
cgtgtgggtg ttttgcgtgg cggctgcgag gttgagatct ggaagcgcgc ccagtccgaa   1320
aacaaggacg tctcaaccgt cgttgattct tcgggtaacc gcatcgtccg cgcgggtggg   1380
caagcgacca aggtcgtcca gcctgttccg ggtgctcagg ccgcgtga              1428

<210> SEQ ID NO 14
<211> LENGTH: 1997
<212> TYPE: DNA
<213> ORGANISM: Leptosphaeria nodorum

<400> SEQUENCE: 14
cccgattcat taatgcagct ggcacgacag gtttcccgac tggaaagcgg gcagtgagcg     60
caacgcaatt aatgtgagtt agctcactca ttaggcaccc caggctttac actttatgct    120
tccggctcgt atgttgtgtg gaattgtgag cggataacaa tttcacacag gaaacagcta    180
tgaccatgat tacgccaagc tcgaaattaa ccctcactaa agggaacaaa agctggagct    240
ccaccgcggt ggcggccgct ctagaactag tggatccccc gggctgcagg aattcggcac    300
gagtatgcct tcccaccagg ctgttgctgg catgcaggcc atcgacccg  agtttgtcaa    360 gcagccgtct cctatggcga gcacctcgga gcccaaccgc aactccaagt acgatcctaa    420
gaagccgcac attacagaca tgcccatcac gcggtcaaac tggtaccagc atgtcaactg    480
gctcaacgtc atcttcatca tcggcgtgcc ctctcgctgg ctgcgtcgccg ccttctggac    540 ccctctgcag tggaagaccg ctgcgtgggc tgtcatctac tatttctgga ctggcctcgg    600
tatcaccgcc ggataccatc gtctctgggc acacaagtca tacaacgccg gtcttcctct    660
gaggatctgg ctcgccgccg tcggcgctgg tgctgttgag ggttccatcc gctggtggag    720
ccgtgaccac cgcgcccacc accgctacac cgacaccaac aaggacccct acagtgtccg    780
caagggcctt ctctacagcc atctcggatg gatggtcatg aagcagaacc ccaagcgtat    840
cggccgcacc gacatcaccg acttgaacga ggaccccgtt gtcgtctggc agcacaagaa    900
ctacatcaag gccgtcgtca ccatgggctt gatcttttccc tctgccgtcg ccggtctcat    960
gtggggcgat tggatgggtg gcttcatcta cgctggtatc ctccgtatct tcttcgtcca   1020
gcaggccacc ttctgcgtca actcgcttgc tcactggctc ggtgaccagc ccttcgacga   1080
ccgcaactct cctcgtgacc acgtcattac cgctcttgtc actctcggag agggctacca   1140
caacttccac cacagagttcc cctccgacta ccgcaacgcc atcgagtggc accagtacga   1200
ccctaccaag tggtccatct ggctgtggag caagctcggc ctcgcctcca acctcaagca   1260
gttccgctcc aacgaaatcg agaagggtcg tgtccagcag ctccagaaga agattgacca   1320
gaagcgcgcc aagctcgact ggggtgtccc tctcgaccag ctgcctgtca tagaatggga   1380
cgactatgtc gagcaggcca agaacggccg tggtctcatc gctgtcgctg gtgtcgttca   1440
tgacgttacc gacttcatca acgagcaccc cggtggcaag acgcttatca agagcggcgt   1500
tggcaaggat gccaccgcca tgttcaacgg cggtgtctac ttccactcca acggagccca   1560
caacctcctt tctaccatga gggttggtgt catccgcggt ggctgtgaag ttgagatctg   1620
```

```
gaagcgcgct cagcgtgaga acaaggatgt cggtctggtc ctggacgacg caggcaaccc    1680
aatcatcagg gctggtaacc agattaccaa ggttgcgcaa cccattcaga gtgctagtgc    1740
agcatagatt ggatcttcat cttcacgagc gatgtatggc gtttggttgt ctctcttcct    1800
tggcggacag agtaatattc aatttcttag cgatcgttag aaagcatcat ggttacgatg    1860
ctcagtcatg ttagatggcg tatgtttgta gccttcctcg agtgattggs tatgaaaagt    1920
agcctcacgg cctagaccaa gaatgaaaac attcacgatt tcagaaaaaa aaaaaaaaa    1980 aaactcgagg gggggcc                                                   1997
```

<210> SEQ ID NO 15
<211> LENGTH: 1370
<212> TYPE: DNA
<213> ORGANISM: Leptosphaeria nodorum

<400> SEQUENCE: 15

```
ggatccatgg cggccttgga cagcattcca gaggataagg ctacctcgtc gaaatcgact      60
catattcaat atcaagaagt aacttttcgg aactggtata agaagataaa ttggctcaac     120
acgacgctgg tggtgctcat acccgctctt ggactctacc taaacgcgcac cacgccactt    180 acacgaccta cgctcatctg gtccgtcctg tactacttct gcacagcttt cggcatcaca    240
ggcggatatc atcgactatg gagtcatcgc agctactccg ctcgtctacc gctacgctta    300
ttcctagcct tcacaggcgc cggagccatc caaggtagtg ctcgatggtg gagcgcaaat    360
caccgcgccc accaccgatg gaccgacaca atgaaggacc cctactccgt tatgcgcggc    420
ctattattct cgcacatcgg atggatggta ttgaacagcg accccaaagt caaaggccga    480
acagacgtca gtgatctcga cagcgacccc gtcgtagtct ggcagcacaa gcactacggc    540
aagtgcctgc tgttcgccgc gtggatattc cccatgatcg tagccggcct cggatgggga    600
gattggtggg gaggccttgt ctacgccggc atcattcgag cgtgtttcgt ccagcaggcg    660
acattttgcg tgaactctct cgcgcattgg atcggcgagc agccgttcga cgacagacgc    720
acgcctcgag accacgtttt gacagcgttg gtaacgatgg gagaaggata tcataacttc    780
caccacgaat tcccaagcga ttatcgcaac gcgatcatct ggtaccaata cgaccctacc    840
aaatggctca tttacctctt ctccctcggc cccttccccc tcgcatactc gctcaaaacc    900
ttccggtcca atgagattga aaagggcgg ttgcaacaac aacaaaagc cctgacaag    960 aagcgctcag gacttgattg gggcctaccc ctcttccaac tccctgtcat atcgtgggac    1020
gacttccaag cgcgttgcaa agagtccggc gagatgctgg ttgctgtcgc aggtgtgatt    1080
cacgacgtca gccagtttat tgaagatcac cctggaggca ggagtttgat tcggagtgcg    1140
gtgggcaaag atgggacagg gatgtttaat ggaggcgtat atgagcacag taatgcggcg    1200
cataatctgt tgtcgacaat gagggtggga gtgcttagag gtgggcagga ggtggaggtg    1260
tggaagaagc agagagtgga tgttttaggg aagagcgaca ttttgagaca ggttacgcgg    1320
gtggagaggt tggttgaggg ggctgtggct gcgtagctaa ctgaccatgg                1370
```

<210> SEQ ID NO 16
<211> LENGTH: 1428
<212> TYPE: DNA
<213> ORGANISM: Magnaporthe grisea

<400> SEQUENCE: 16

```
atggcttcgt catcttcctc cgtgccggag ttggctgccg ccttccctga tggcactacc    60
```

-continued

```
gacttcaagc ccatgaggaa caccaagggc tacgacgtca gcaagccgca catttccgag     120
acacctatga cactcaagaa ctggcataag cacgtcaact ggctcaacac caccttcatc     180
ttgtttgtgc ccctggctgg tctcatatcc acttactggg tccctctgca gtggaagacg     240
gctgtatggg ctgtcgtcta ctacttcaac accggcctgg gaattactgc cggttaccac     300
cgactttggg ctcacagctc gtacaaggcc tcgcttccgc tcaaaatcta ccttgccgcc     360
gttggcgctg gtgccgtcga gggctccatc agatggtggt ccaacggtca ccgcgcacac     420
caccgataca ccgataccga aaggacccc tactcagtcc gcaagggtct cctgtactca      480
cacatgggat ggatgcttct gaagcagaac cccaagaagc agggccgcac cgacatcacc     540
gacctgaacg aggaccccgt tgtcgtttgg cagcaccgca acttcctcaa gtgtgttatc     600
ttcatggccc tcgtcttccc cacacttgtg gctggcttg gctgggtga ctactgggga      660
ggtttcatct acggaggtat tctgcgtgtc ttcttcgtcc agcaggccac cttctgcgtc     720
aactcgcttg cccactggct cggtgaccag cctttcgacg atcgcaactc gccgcgtgat     780
cacgtcatca cagccctggt cacccttgga gagggatacc acaacttcca ccacgagttc     840
ccttcggact accgcaacgc tattgagtgg taccagtatg accccaccaa gtggtcaatc     900
tggatctgga agcagcttgg tcttgcccac aacctgaagc agttccgcca aaacgagatt     960
gagaagggac gcgtccagca gctgcagaag aagctcgacc agaagcgcgc caagcttgat    1020
tggggtattc ccttggagca gcttcccgtt gttagctggg atgactttgt tgagcagtcc    1080
aagaacggaa aggcttggat tgcagttgcc ggtgtcatcc acgatgttgg tgacttcatc    1140
aaggaccacc ctggtggcag agctctcatc aactcggcca ttggcaagga cgcaaccgca    1200
atcttcaacg gcggtgttta caaccactcc aacgccgctc acaacctgct ctcgactatg    1260
cgtgtgggtg ttttgcgtgg cggctgcgag gttgagatct ggaagcgcgc ccagtccgaa    1320
aacaaggacg tctcaaccgt cgttgattct tcgggtaacc gcatcgtccg cgcgggtggg    1380
caagcgacca aggtcgtcca gcctgttccg ggtgctcagg ccgcgtga               1428
```

<210> SEQ ID NO 17
<211> LENGTH: 1062
<212> TYPE: DNA
<213> ORGANISM: Helicoverpa zea

<400> SEQUENCE: 17

```
atggctccaa atatatcgga ggatgtgaac ggggtgctct tcgagagtga tgcagcgacg      60
ccggacctgg cgctgtccac gccgcctgtg cagaaggctg acaacaggcc caagcaactg     120
gtgtggagga acatactact gttcgcgtat cttcacttag cggctctta cggaggttat     180
ctgttcctct tctcagctaa atggcagaca gacatatttg cctacatcct gtatgtgatc     240
tccgggcttg gtatcacggc tggagcacat cgcctgtggg cccacaagtc ctacaaagct     300
aaatggcctc tccgagttat cctggtcatc tttaacacag tggcattcca ggatgccgct     360
atggactggg cgcgcgacca ccgcatgcat cacaagtact cggaaaccga tgctgatcct     420
cataatgcga cccgaggatt cttcttctct cacattggct ggctgcttgt caggaaacat     480
cccgacctta aggagaaggg caagggactg gacatgagcg acttacttgc tgaccccatt     540
ctcaggttcc agaaaaaata ctacctgatc ctgatgccct ggcttgctt cgtgatgcct     600
accgtgattc ctgtgtactt ctggggtgaa acctggacca cgcattctt tgtggcggcc     660
atgttccgct acgcgttcat cctaaatgtg acgtggctcg tcaactctgc cgctcacaag     720
tgggagacag agccctacga caaaagcatt aagccttccg aaaacttgtc ggtcgccatg     780
```

```
ttcgctctcg gagaaggatt ccacaactac caccacactt tcccttggga ctacaaaact    840
gctgagctgg gcaacaacaa actcaacttc actaccacct ttattaactt cttcgctaaa    900
attggctggg cttacgacct gaagacagtg tctgatgata tcgtcaagaa cagggtgaag    960
cgcactggtg acggctccca ccacctgtgg ggctggggag acgaaaatca atccaaagaa   1020
gaaattgatg ccgctatcag aatcaatcct aaggacgatt aa                      1062
```

<210> SEQ ID NO 18
<211> LENGTH: 1350
<212> TYPE: DNA
<213> ORGANISM: Leptosphaeria nodorum

<400> SEQUENCE: 18

```
atggcggcct tggacagcat tccagaggat aaggctacct cgtcgaaatc gactcatatt     60
caatatcaag aagtaacttt tcggaactgg tataagaaga taaattggct caacacgacg    120
ctggtggtgc tcataccgc tcttggactc tacctaacac gcaccacgcc acttacacga    180
cctacgctca tctggtccgt cctgtactac ttctgcacag ctttcggcat cacaggcgga    240
tatcatcgac tatggagtca tcgcagctac tccgctcgtc taccgctacg cttattccta    300
gccttcacag gcgccggagc catccaaggt agtgctcgat ggtggagcgc aaatcaccgc    360
gcccaccacc gatggaccga cacaatgaag gaccccctact ccgttatgcg cggcctatta    420
ttctcgcaca tcggatggat ggtattgaac agcgacccca aagtcaaagg ccgaacagac    480
gtcagtgatc tcgacagcga ccccgtcgta gtctggcagc acaagcacta cggcaagtgc    540
ctgctgttcg ccgcgtggat attccccatg atcgtagccg gcctcggatg gggagattgg    600
tggggaggcc ttgtctacgc cggcatcatt cgagcgtgtt tcgtccagca ggcgacattt    660
tgcgtgaact ctctcgcgca ttggatcggc gagcagccgt tcgacgacag acgcacgcct    720
cgagaccacg ttttgacagc gttggtaacg atgggagaag gatatcataa cttccaccac    780
gaattcccaa gcgattatcg caacgcgatc atctggtacc aatacgaccc taccaaatgg    840
ctcatttacc tcttctccct cggcccctcc ccctcgcat actcgctcaa aaccttccgg    900
tccaatgaga ttgaaaaagg gcggttgcaa caacaacaaa aagcccctgga caagaagcgc    960 tcaggacttg attggggcct accctctctc caactccctg tcatatcgtg ggacgacttc   1020
caagcgcgtt gcaaagagtc cggcgagatg ctggttgctg tcgcaggtgt gattcacgac   1080
gtcagccagt ttattgaaga tcaccctgga ggcaggagtt tgattcggag tgcggtgggc   1140
aaagatggga cagggatgtt taatggaggc gtatatgagc acagtaatgc ggcgcataat   1200
ctgttgtcga caatgagggt gggagtgctt agaggtgggc aggaggtgga ggtgtggaag   1260
aagcagagag tggatgttttt agggaagagc gacattttga acaggttac gcgggtggag   1320 aggttggttg aggggctgt ggctgcgtag                                      1350
```

<210> SEQ ID NO 19
<211> LENGTH: 1428
<212> TYPE: DNA
<213> ORGANISM: Artificial Sequence
<220> FEATURE:
<223> OTHER INFORMATION: Canola-optimized desaturase sequence

<400> SEQUENCE: 19

```
atggccagca gttcttcaag tgtgccagaa cttgccgcag ctttccctga tgggacaacg     60
gacttcaaac ccatgaggaa caccaaaggc tatgatgtct ccaaacctca catctctgaa    120
```

| | |
|---|---|
| acaccgatga ctttgaagaa ctggcacaaa catgtgaact ggctcaacac cacattcatt | 180 |
| ctctttgttc cactggctgg gttgatctca acctattggg ttcctcttca atggaaaact | 240 |
| gcagtgtggg cagttgtgta ctacttcaac actggacttg ggatcactgc tggctaccat | 300 |
| agattgtggg cacattcctc ttacaaggcc agcttgcctc tcaaaatcta ccttgccgca | 360 |
| gttggtgctg gagccgttga aggttccata agatggtgga gcaacggaca cagagcacat | 420 |
| cacagataca cagacacaga gaaagatcct tactcagtga ggaagggatt gctctacagc | 480 |
| cacatgggtt ggatgctctt gaagcagaat ccaaagaagc aagggaggac ggacattact | 540 |
| gatctgaatg aggacccagt tgtggtctgg caacatagga actttctcaa gtgtgtgatc | 600 |
| ttcatggctt tggtctttcc caccttgtt gctggcctgg gatggggaga ctactgggga | 660 |
| ggtttcatct atggagggat cttgagagtg ttctttgttc agcaagccac cttctgtgtc | 720 |
| aactcacttg cacattggct tggtgatcaa ccgtttgatg acagaaactc tccacgtgac | 780 |
| catgtcataa ctgctcttgt cacgctgggt gaaggctatc acaactttca ccatgagttt | 840 |
| ccgtcagact atagaaatgc gattgagtgg tatcagtatg accccacgaa gtggagcatt | 900 |
| tggatttgga agcaacttgg acttgctcac aatctcaagc agttcagaca gaatgagata | 960 |
| gagaagggaa gggttcaaca gttgcagaag aaactggatc agaagagagc gaaacttgat | 1020 |
| tggggaatac cgttggaaca actccctgtt gtgtcttggg atgactttgt gaacagtca | 1080 |
| aagaatggca aggcatggat tgctgttgct ggtgtcattc acgatgttgg tgacttcatc | 1140 |
| aaggatcatc ctggtggacg tgctctcatc aactctgcga ttggcaaaga tgccacagcg | 1200 |
| atcttcaatg gaggtgtcta caatcattca atgccgcac acaaccttct ctccaccatg | 1260 |
| agggttggtg tcctccgtgg agggtgcgaa gtggagatat ggaaacgtgc tcaaagtgag | 1320 |
| aacaaagatg tctctactgt ggttgatagt tctggcaacc gtattgtgag agctggtgga | 1380 |
| caagctacca agtggttca gccagtccct ggtgctcaag cagcttga | 1428 |

<210> SEQ ID NO 20
<211> LENGTH: 1062
<212> TYPE: DNA
<213> ORGANISM: Artificial Sequence
<220> FEATURE:
<223> OTHER INFORMATION: Canola-optimized desaturase sequence

<400> SEQUENCE: 20

| | |
|---|---|
| atggctccca acatttctga ggatgtcaat ggtgttcttt ttgagtcaga tgcggcaacc | 60 |
| cctgatttgg ctcttttccac accacctgtg caaaaagctg acaacagacc caagcaactt | 120 |
| gtgtggagga acattttgct tttcgcttac ttgcacctcg cagctctcta cggaggctat | 180 |
| ttgtttctct tcagtgcaaa atggcagacc gacattttcg cttacattct ttatgtcatc | 240 |
| tctggactgg ggataactgc tggggcacat agactctggg ctcacaagtc atacaaagcc | 300 |
| aagtggccac tcagagttat actggtcatc ttcaacacgg ttgcctttca agacgctgct | 360 |
| atggattggg ctcgtgacca tagaatgcat acaagtacaa gcgagaccga cgcggaccca | 420 |
| cacaatgcaa cgagaggttt cttcttctct cacattggct ggcttcttgt taggaaacat | 480 |
| cctgatctga agaaaaagg gaagggactc gacatgagtg atctccttgc tgatccaata | 540 |
| ctccgttttc agaagaagta ctatctgatc ctcatgcctc tggcctgttt tgtgatgcca | 600 |
| accgttatcc cggtttactt ttggggagaa acttggacaa atgctttctt cgtggcagcc | 660 |
| atgttccgtt atgctttcat cctgaatgtt acctggttgg tgaactctgc cgcacacaag | 720 |
| tggggagaca aaccctatga caagtccatc aagccttccg aaaaccttc agttgcgatg | 780 |

```
tttgctttgg gagaaggatt tcacaattac catcacactt ttccgtggga ctacaagaca    840
gcagagcttg gaaacaacaa gttgaacttc acaacaacgt tcatcaattt ctttgcgaaa    900
atcggttggg cctatgattt gaagactgtg agtgatgaca ttgtcaagaa cagggtcaag    960
agaactggcg atggaagcca tcatctctgg ggctggggtg atgagaatca gagcaaagaa   1020
gagatagatg cagccattag gatcaaccct aaagacgatt ga                       1062
```

<210> SEQ ID NO 21
<211> LENGTH: 1350
<212> TYPE: DNA
<213> ORGANISM: Artificial Sequence
<220> FEATURE:
<223> OTHER INFORMATION: Canola-optimized desaturase sequence

<400> SEQUENCE: 21

```
atggctgcac ttgatagcat ccctgaggac aaagcaacta gctccaagtc aacccacata    60
cagtaccaag aggtcacgtt taggaactgg tacaagaaaa tcaactggct caacacgacc   120
cttgttgtcc tcattcctgc tcttgggttg tacttgacga gaaccacacc tctcaccaga   180
cctaccctca tttggtctgt tctctactat ttctgtacag cgtttggcat cactggtggc   240
taccacagac tttggtccca taggtcttac agtgcgaggt tgccattgag actcttcctg   300
gctttcactg agctggtgc gatccaaggt tctgcaagat ggtggtcagc caatcatagg   360
gcacatcacc gttggacgga caccatgaag gaccctact ctgtgatgag aggactgctg   420
ttctcccaca taggttggat ggttctcaac tctgatccaa aggtcaaagg cagaacagat   480
gtttctgatc ttgactctga tcccgtcgtt gtgtggcaac acaaacacta tggcaagtgt   540
ttgctctttg ccgcttggat ctttccgatg atagtggctg gctgggttg gggagattgg   600 tggggtggac ttgtctatgc tggcatcata cgtgcctgct tgttcagca agccactttc   660 tgtgtcaact cattggcaca ttggataggt gaacaaccgt ttgatgacag acgtactcca   720
agggatcatg ttctgactgc gttggtcaca atgggagaag gataccacaa cttccaccat   780
gagtttccga gtgactacag aaatgccatc atttggtatc agtatgaccc tacaaagtgg   840
ctcatctatc tcttcagctt gggtcccttc ccattggcct actctctcaa gaccttccgt   900
tccaatgaga ttgagaaagg aaggcttcag caacagcaaa aggctcttga caagaaaaga   960
agtggtcttg attggggact tcctctcttc cagcttccag tgatctcatg ggatgacttt   1020
caagctcgtt gcaaagaaag tggagagatg cttgttgctg ttgctggagt gatccatgat   1080
gtctcccagt tcattgaaga tcatcctggt gggaggagcc tcattagaag tgctgttggg   1140
aaagatggga ctggcatgtt caatggtgga gtgtatgaac attcaaacgc cgcacacaac   1200
ttgctgagca caatgagagt tggagtcttg agaggtggca agaagtgga ggtttggaag   1260 aaacagaggg tggatgttct tgggaagtca gacattcttc gtcaagtgac aagggtggag   1320
cgtctggtgg aaggagctgt tgcagcgtga                                    1350
```

<210> SEQ ID NO 22
<211> LENGTH: 1350
<212> TYPE: DNA
<213> ORGANISM: Artificial Sequence
<220> FEATURE:
<223> OTHER INFORMATION: Canola-optimized desaturase

<400> SEQUENCE: 22

```
atggctgctc ttgattctat cccagaggat aaggctacct cttctaagtc tacccacatc    60
```

| | |
|---|---|
| caataccaag aagttacctt caggaactgg tacaagaaga tcaactggct taacaccacc | 120 |
| cttgttgttc ttatcccagc tcttggactt taccttacca ggaccacccc acttaccagg | 180 |
| ccaaccctta tctggtctgt tctttactac ttctgcaccg ctttcggaat aaccggagga | 240 |
| taccacaggc tttggtctca caggtcttac tctgctaggc ttccacttag gcttttcctt | 300 |
| gctttcaccg gagctggagc tatccaagga tctgctagat ggtggtctgc taaccacagg | 360 |
| gctcaccaca ggtggaccga taccatgaag acccatact ctgttatgag gggacttctt | 420 |
| ttctctcaca tcggatggat ggttcttaac tctgatccaa aggttaaggg aaggaccgat | 480 |
| gtttctgatc ttgattctga tccagttgtt gtttggcaac acaagcacta cggaaagtgc | 540 |
| cttcttttcg ctgcttggat ctcccaatg atcgttgctg acttggatg gggagattgg | 600 |
| tggggaggac ttgtttacgc tggaatcatc agggcttgct tcgttcaaca agctaccttc | 660 |
| tgcgttaact ctcttgctca ctggatcgga gagcaaccat tcgacgatag gaggaccca | 720 |
| aggatcacg ttcttaccgc tcttgttacc atgggagagg gataccacaa cttccaccac | 780 |
| gagttcccat ctgattacag gaacgctatc atctggtacc aatacgatcc aaccaagtgg | 840 |
| cttatctacc ttttctctct tggaccattc ccacttgctt actctcttaa gaccttcagg | 900 |
| tctaacgaga tcgagaaggg aaggcttcaa caacaacaaa aggctcttga taagaagagg | 960 |
| tctggacttg attggggact tccacttttc caacttccag ttatctcttg ggatgatttc | 1020 |
| caagctaggt gcaaggagtc tggagagatg cttgttgctg ttgctggagt tatccacgat | 1080 |
| gtttctcaat tcatcgagga tcacccagga ggaaggtctc ttatcaggtc tgctgttgga | 1140 |
| aaggatggaa ccggaatgtt caacggagga gtttacgagc actctaacgc tgctcacaac | 1200 |
| cttcttttcta ccatgagggt tggagttctt aggggaggac aagaggttga ggtttggaag | 1260 |
| aagcaaaggg ttgatgttct tggaaagtca gatatcctta ggcaagttac cagggttgag | 1320 |
| aggcttgttg agggagctgt tgctgcttga | 1350 |

<210> SEQ ID NO 23
<211> LENGTH: 1062
<212> TYPE: DNA
<213> ORGANISM: Artificial Sequence
<220> FEATURE:
<223> OTHER INFORMATION: Canola-optimized desaturase

<400> SEQUENCE: 23

| | |
|---|---|
| atggctccaa acatctctga ggatgttaac ggagttcttt tcgagtctga tgctgctacc | 60 |
| ccagatcttg ctcttttctac cccaccagtt caaaaggctg ataacaggcc aaagcaactt | 120 |
| gtttggagga acatccttct tttcgcttac cttcaccttg ctgctcttta cggaggatac | 180 |
| cttttccttt tctctgctaa gtggcaaaacc gatatcttcg cttacatcct ttacgttatc | 240 |
| tctggacttg aataaccgc tggagcacac aggctttggg ctcacaagtc ttacaaggct | 300 |
| aagtggccac ttagggttat ccttgttatc ttcaacaccg ttgctttcca agacgctgct | 360 |
| atggattggg ctagggatca caggatgcac acaagtact ctgagaccga cgctgatcca | 420 |
| cacaacgcta ccaggggatt cttcttctct cacatcggat ggcttcttgt taggaagcac | 480 |
| ccagatctta aggagaaggg aaagggactt gatatgtctg atcttcttgc tgatccaatc | 540 |
| cttaggttcc aaaagaagta ctaccttatc cttatgccac ttgcttgctt cgttatgcca | 600 |
| accgttatcc cagtttactt ctggggagag acctggacca acgctttctt cgttgctgct | 660 |
| atgttcaggt acgctttcat ccttaacgtt acctggcttg ttaactctgc tgctcacaag | 720 |
| tggggagata agccatacga taagtctatc aagccatctg agaacctttc tgttgctatg | 780 |

```
ttcgctcttg gagagggatt ccacaactac caccacacct tcccatggga ttacaagacc    840
gctgagcttg gaaacaacaa gcttaacttc accaccacct tcatcaactt cttcgctaag    900
atcggatggg cttacgatct taagaccgtt tctgatgata tcgttaagaa cagggttaag    960
aggaccggag atggatcaca ccacctttgg ggatggggag atgagaacca atctaaggag   1020
gagatcgatg ctgctatcag gatcaaccca aaggatgatt ga                      1062
```

<210> SEQ ID NO 24
<211> LENGTH: 1368
<212> TYPE: DNA
<213> ORGANISM: Aspergillus nidulans

<400> SEQUENCE: 24

```
atgtctgctc caaccgctga catcagggct agggctccag aggctaagaa ggttcacatc     60
gctgataccg ctatcaacag gcacaattgg tacaagcacg tgaactggct caacgtcttc    120
ctcatcatcg gaatcccact ctacggatgc atccaagctt tctgggttcc acttcaactc    180
aagaccgcta tctgggctgt gatctactac ttcttcaccg gacttggaat caccgctgga    240
taccacaggc tttgggctca ctgctcttac tctgctactc ttccacttag gatctggctt    300
gctgctgttg gaggaggagc tgttgaggga tctatcagat ggtgggctag ggatcacagg    360
gctcatcata ggtacaccga taccgacaag gacccatact ctgttaggaa gggacttctc    420
tactctcacc ttggatggat ggtgatgaag cagaacccaa agaggatcgg aaggaccgac    480
atctctgatc tcaacgagga cccagttgtt gtttggcaac acaggaacta cctcaaggtt    540
gtgttcacca tgggacttgc tgttccaatg cttgttgctg acttggatg gggagattgg     600 cttggaggat tcgtgtacgc tggaatcctt aggatcttct tcgttcaaca agctaccttc    660
tgcgtgaact ctcttgctca ctggcttgga gatcaaccat tcgatgatag gaactctcct    720
agggatcacg tgatcaccgc tcttgttacc cttggagagg gataccacaa cttccaccac    780
gagttcccat ctgactacag gaacgctatc gagtggcacc agtacgatcc taccaagtgg    840
tctatctggg cttggaagca acttggattg gcttacgatc tcaagaagtt cagggctaac    900
gagatcgaga agggaagggt tcaacaactt cagaagaagc ttgataggaa gagggctact    960
cttgattggg aaccccact tgatcaactt ccagtgatgg aatgggatga ctacgttgag   1020
caagctaaga acgaagggg acttgttgct atcgctggag ttgttcacga tgttaccgac   1080
ttcatcaagg atcacccagg aggaaaggct atgatctctt ctggaatcgg aaaggatgct   1140
accgctatgt tcaacggagg agtgtactac cactctaacg cagctcacaa ccttcttagc   1200
accatgaggg tgggagtgat caggggagga tgcgaggttg agatctggaa gagggctcag   1260
aaggagaacg ttgagtacgt tagggatgga tctggacaaa gggtgatcag ggctggagag   1320
caaccaacca agatcccaga gccaatccca accgctgatg ctgcttga              1368
```

<210> SEQ ID NO 25
<211> LENGTH: 1368
<212> TYPE: DNA
<213> ORGANISM: Artificial Sequence
<220> FEATURE:
<223> OTHER INFORMATION: AnD9DS v3 silent mutant

<400> SEQUENCE: 25

```
atgtctgctc caaccgctga catcagggct agggctccag aggctaagaa ggttcacatc     60
gctgataccg ctatcaacag gcacaattgg tacaagcacg tgaactggct caacgtcttc    120
```

```
ctcatcatcg gaatcccact ctacggatgc atccaagctt tctgggttcc acttcaactc    180
aagaccgcta tctgggctgt gatctactac ttcttcaccg acttggaat caccgctgga     240
taccacaggc tttgggctca ctgctcatac tctgctactc ttccacttag gatctggctt    300
gctgctgttg gaggaggagc tgttgaggga tctatcagat ggtgggctag ggatcacagg    360
gctcatcata ggtacaccga taccgacaag gacccatact ctgttaggaa gggacttctc    420
tactctcacc ttggatggat ggtgatgaag cagaacccaa agaggatcgg aaggaccgac    480
atctctgatc tcaacgagga cccagttgtt gtttggcaac acaggaacta cctcaaggtt    540
gtgttcacca tgggacttgc tgttccaatg cttgttgctg acttggatg gggagattgg     600
cttggaggat tcgtgtacgc tggaatcctt aggatcttct tcgttcaaca agctaccttc    660
tgcgtgaact ctcttgctca ctggcttgga gatcaaccat tcgatgatag gaactctcct    720
agggatcacg tgatcaccgc tcttgttacc cttggagagg gataccacaa cttccaccac    780
gagttcccat ctgactacag gaacgctatc gagtggcacc agtacgatcc taccaagtgg    840
tctatctggg cttggaagca acttggattg gcttacgatc tcaagaagtt cagggctaac    900
gagatcgaga agggaagggt tcaacaactt cagaagaagc ttgataggaa gagggctact    960
cttgattggg aaccccact tgatcaactt ccagtgatgg aatgggatga ctacgttgag    1020
caagctaaga acggaagggg acttgttgct atcgctggag ttgttcacga tgttaccgac   1080
ttcatcaagg atcacccagg aggaaaggct atgatctctt ctggaatcgg aaaggatgct   1140
accgctatgt tcaacggagg agtgtactac cactctaacg cagctcacaa ccttcttagc   1200
accatgaggg tgggagtgat caggggagga tgcgaggttg agatctggaa gagggctcag   1260
aaggagaacg ttgagtacgt tagggatgga tctggacaaa gggtgatcag gctggagag    1320
caaccaacca agatcccaga gccaatccca accgctgatg ctgcttga                1368
```

<210> SEQ ID NO 26
<211> LENGTH: 475
<212> TYPE: PRT
<213> ORGANISM: Magnaporthe grisea

<400> SEQUENCE: 26

```
Met Ala Ser Ser Ser Ser Val Pro Glu Leu Ala Ala Phe Pro
1               5                   10                  15

Asp Gly Thr Thr Asp Phe Lys Pro Met Arg Asn Thr Lys Gly Tyr Asp
            20                  25                  30

Val Ser Lys Pro His Ile Ser Glu Thr Pro Met Thr Leu Lys Asn Trp
        35                  40                  45

His Lys His Val Asn Trp Leu Asn Thr Thr Phe Ile Leu Phe Val Pro
    50                  55                  60

Leu Ala Gly Leu Ile Ser Thr Tyr Trp Val Pro Leu Gln Trp Lys Thr
65                  70                  75                  80

Ala Val Trp Ala Val Tyr Tyr Phe Asn Thr Gly Leu Gly Ile Thr
                85                  90                  95

Ala Gly Tyr His Arg Leu Trp Ala His Ser Ser Tyr Lys Ala Ser Leu
            100                 105                 110

Pro Leu Lys Ile Tyr Leu Ala Ala Val Gly Ala Gly Ala Val Glu Gly
        115                 120                 125

Ser Ile Arg Trp Trp Ser Asn Gly His Arg Ala His His Arg Tyr Thr
    130                 135                 140

Asp Thr Glu Lys Asp Pro Tyr Ser Val Arg Lys Gly Leu Leu Tyr Ser
145                 150                 155                 160
```

```
His Met Gly Trp Met Leu Leu Lys Gln Asn Pro Lys Lys Gln Gly Arg
                165                 170                 175

Thr Asp Ile Thr Asp Leu Asn Glu Asp Pro Val Val Trp Gln His
            180                 185                 190

Arg Asn Phe Leu Lys Cys Val Ile Phe Met Ala Leu Val Phe Pro Thr
                195                 200                 205

Leu Val Ala Gly Leu Gly Trp Gly Asp Tyr Trp Gly Gly Phe Ile Tyr
            210                 215                 220

Gly Gly Ile Leu Arg Val Phe Phe Val Gln Gln Ala Thr Phe Cys Val
225                 230                 235                 240

Asn Ser Leu Ala His Trp Leu Gly Asp Gln Pro Phe Asp Arg Asn
                245                 250                 255

Ser Pro Arg Asp His Val Ile Thr Ala Leu Val Thr Leu Gly Glu Gly
                260                 265                 270

Tyr His Asn Phe His His Glu Phe Pro Ser Asp Tyr Arg Asn Ala Ile
                275                 280                 285

Glu Trp Tyr Gln Tyr Asp Pro Thr Lys Trp Ser Ile Trp Ile Trp Lys
            290                 295                 300

Gln Leu Gly Leu Ala His Asn Leu Lys Gln Phe Arg Gln Asn Glu Ile
305                 310                 315                 320

Glu Lys Gly Arg Val Gln Gln Leu Gln Lys Lys Leu Asp Gln Lys Arg
                325                 330                 335

Ala Lys Leu Asp Trp Gly Ile Pro Leu Glu Gln Leu Pro Val Val Ser
                340                 345                 350

Trp Asp Asp Phe Val Glu Gln Ser Lys Asn Gly Lys Ala Trp Ile Ala
                355                 360                 365

Val Ala Gly Val Ile His Asp Val Gly Asp Phe Ile Lys Asp His Pro
            370                 375                 380

Gly Gly Arg Ala Leu Ile Asn Ser Ala Ile Gly Lys Asp Ala Thr Ala
385                 390                 395                 400

Ile Phe Asn Gly Gly Val Tyr Asn His Ser Asn Ala Ala His Asn Leu
                405                 410                 415

Leu Ser Thr Met Arg Val Gly Val Leu Arg Gly Gly Cys Glu Val Glu
                420                 425                 430

Ile Trp Lys Arg Ala Gln Ser Glu Asn Lys Asp Val Ser Thr Val Val
            435                 440                 445

Asp Ser Ser Gly Asn Arg Ile Val Arg Ala Gly Gln Ala Thr Lys
            450                 455                 460

Val Val Gln Pro Val Pro Gly Ala Gln Ala Ala
465                 470                 475

<210> SEQ ID NO 27
<211> LENGTH: 353
<212> TYPE: PRT
<213> ORGANISM: Helicoverpa zea

<400> SEQUENCE: 27

Met Ala Pro Asn Ile Ser Glu Asp Val Asn Gly Val Leu Phe Glu Ser
1               5                   10                  15

Asp Ala Ala Thr Pro Asp Leu Ala Leu Ser Thr Pro Val Gln Lys
                20                  25                  30

Ala Asp Asn Arg Pro Lys Gln Leu Val Trp Arg Asn Ile Leu Leu Phe
                35                  40                  45

Ala Tyr Leu His Leu Ala Ala Leu Tyr Gly Gly Tyr Leu Phe Leu Phe
```

```
            50                  55                  60
Ser Ala Lys Trp Gln Thr Asp Ile Phe Ala Tyr Ile Leu Tyr Val Ile
 65                  70                  75                  80

Ser Gly Leu Gly Ile Thr Ala Gly Ala His Arg Leu Trp Ala His Lys
                 85                  90                  95

Ser Tyr Lys Ala Lys Trp Pro Leu Arg Val Ile Leu Val Ile Phe Asn
                100                 105                 110

Thr Val Ala Phe Gln Asp Ala Ala Met Asp Trp Ala Arg Asp His Arg
                115                 120                 125

Met His His Lys Tyr Ser Glu Thr Asp Ala Asp Pro His Asn Ala Thr
            130                 135                 140

Arg Gly Phe Phe Ser His Ile Gly Trp Leu Leu Val Arg Lys His
145                 150                 155                 160

Pro Asp Leu Lys Glu Lys Gly Lys Gly Leu Asp Met Ser Asp Leu Leu
                165                 170                 175

Ala Asp Pro Ile Leu Arg Phe Gln Lys Lys Tyr Tyr Leu Ile Leu Met
                180                 185                 190

Pro Leu Ala Cys Phe Val Met Pro Thr Val Ile Pro Val Tyr Phe Trp
                195                 200                 205

Gly Glu Thr Trp Thr Asn Ala Phe Phe Val Ala Ala Met Phe Arg Tyr
210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Leu
                245                 250                 255

Ser Val Ala Met Phe Ala Leu Gly Glu Gly Phe His Asn Tyr His His
                260                 265                 270

Thr Phe Pro Trp Asp Tyr Lys Thr Ala Glu Leu Gly Asn Asn Lys Leu
                275                 280                 285

Asn Phe Thr Thr Thr Phe Ile Asn Phe Phe Ala Lys Ile Gly Trp Ala
                290                 295                 300

Tyr Asp Leu Lys Thr Val Ser Asp Asp Ile Val Lys Asn Arg Val Lys
305                 310                 315                 320

Arg Thr Gly Asp Gly Ser His His Leu Trp Gly Trp Gly Asp Glu Asn
                325                 330                 335

Gln Ser Lys Glu Glu Ile Asp Ala Ala Ile Arg Ile Asn Pro Lys Asp
                340                 345                 350

Asp

<210> SEQ ID NO 28
<211> LENGTH: 449
<212> TYPE: PRT
<213> ORGANISM: Leptosphaeria nodorum

<400> SEQUENCE: 28

Met Ala Ala Leu Asp Ser Ile Pro Glu Asp Lys Ala Thr Ser Ser Lys
 1               5                  10                  15

Ser Thr His Ile Gln Tyr Gln Glu Val Thr Phe Arg Asn Trp Tyr Lys
                20                  25                  30

Lys Ile Asn Trp Leu Asn Thr Leu Val Val Leu Ile Pro Ala Leu
             35                  40                  45

Gly Leu Tyr Leu Thr Arg Thr Thr Pro Leu Thr Arg Pro Thr Leu Ile
            50                  55                  60

Trp Ser Val Leu Tyr Tyr Phe Cys Thr Ala Phe Gly Ile Thr Gly Gly
```

```
            65                  70                  75                  80
Tyr His Arg Leu Trp Ser His Arg Ser Tyr Ser Ala Arg Leu Pro Leu
                85                  90                  95

Arg Leu Phe Leu Ala Phe Thr Gly Ala Gly Ala Ile Gln Gly Ser Ala
            100                 105                 110

Arg Trp Trp Ser Ala Asn His Arg Ala His His Arg Trp Thr Asp Thr
115                 120                 125

Met Lys Asp Pro Tyr Ser Val Met Arg Gly Leu Leu Phe Ser His Ile
            130                 135                 140

Gly Trp Met Val Leu Asn Ser Asp Pro Lys Val Lys Gly Arg Thr Asp
145                 150                 155                 160

Val Ser Asp Leu Asp Ser Asp Pro Val Val Trp Gln His Lys His
                165                 170                 175

Tyr Gly Lys Cys Leu Leu Phe Ala Ala Trp Ile Phe Pro Met Ile Val
            180                 185                 190

Ala Gly Leu Gly Trp Gly Asp Trp Trp Gly Gly Leu Val Tyr Ala Gly
                195                 200                 205

Ile Ile Arg Ala Cys Phe Val Gln Gln Ala Thr Phe Cys Val Asn Ser
210                 215                 220

Leu Ala His Trp Ile Gly Glu Gln Pro Phe Asp Asp Arg Arg Thr Pro
225                 230                 235                 240

Arg Asp His Val Leu Thr Ala Leu Val Thr Met Gly Glu Gly Tyr His
            245                 250                 255

Asn Phe His His Glu Phe Pro Ser Asp Tyr Arg Asn Ala Ile Ile Trp
                260                 265                 270

Tyr Gln Tyr Asp Pro Thr Lys Trp Leu Ile Tyr Leu Phe Ser Leu Gly
            275                 280                 285

Pro Phe Pro Leu Ala Tyr Ser Leu Lys Thr Phe Arg Ser Asn Glu Ile
            290                 295                 300

Glu Lys Gly Arg Leu Gln Gln Gln Lys Ala Leu Asp Lys Lys Arg
305                 310                 315                 320

Ser Gly Leu Asp Trp Gly Leu Pro Leu Phe Gln Leu Pro Val Ile Ser
                325                 330                 335

Trp Asp Asp Phe Gln Ala Arg Cys Lys Glu Ser Gly Glu Met Leu Val
                340                 345                 350

Ala Val Ala Gly Val Ile His Asp Val Ser Gln Phe Ile Glu Asp His
            355                 360                 365

Pro Gly Gly Arg Ser Leu Ile Arg Ser Ala Val Gly Lys Asp Gly Thr
370                 375                 380

Gly Met Phe Asn Gly Gly Val Tyr Glu His Ser Asn Ala Ala His Asn
385                 390                 395                 400

Leu Leu Ser Thr Met Arg Val Gly Val Leu Arg Gly Gln Glu Val
                405                 410                 415

Glu Val Trp Lys Lys Gln Arg Val Asp Val Leu Gly Lys Ser Asp Ile
                420                 425                 430

Leu Arg Gln Val Thr Arg Val Glu Arg Leu Val Glu Gly Ala Val Ala
            435                 440                 445

Ala

<210> SEQ ID NO 29
<211> LENGTH: 455
<212> TYPE: PRT
<213> ORGANISM: Aspergillus nidulans
```

<400> SEQUENCE: 29

Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
            20                  25                  30

His Val Asn Trp Leu Asn Val Phe Leu Ile Gly Ile Pro Leu Tyr
        35                  40                  45

Gly Cys Ile Gln Ala Phe Trp Val Pro Leu Gln Leu Lys Thr Ala Ile
    50                  55                  60

Trp Ala Val Ile Tyr Tyr Phe Phe Thr Gly Leu Gly Ile Thr Ala Gly
65                  70                  75                  80

Tyr His Arg Leu Trp Ala His Cys Ser Tyr Ser Ala Thr Leu Pro Leu
                85                  90                  95

Arg Ile Trp Leu Ala Ala Val Gly Gly Gly Ala Val Glu Gly Ser Ile
            100                 105                 110

Arg Trp Trp Ala Arg Asp His Arg Ala His His Arg Tyr Thr Asp Thr
        115                 120                 125

Asp Lys Asp Pro Tyr Ser Val Arg Lys Gly Leu Leu Tyr Ser His Leu
    130                 135                 140

Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
                165                 170                 175

Tyr Leu Lys Val Val Phe Thr Met Gly Leu Ala Val Pro Met Leu Val
            180                 185                 190

Ala Gly Leu Gly Trp Gly Asp Trp Leu Gly Gly Phe Val Tyr Ala Gly
        195                 200                 205

Ile Leu Arg Ile Phe Phe Val Gln Gln Ala Thr Phe Cys Val Asn Ser
    210                 215                 220

Leu Ala His Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
                245                 250                 255

Asn Phe His His Glu Phe Pro Ser Asp Tyr Arg Asn Ala Ile Glu Trp
            260                 265                 270

His Gln Tyr Asp Pro Thr Lys Trp Ser Ile Trp Ala Trp Lys Gln Leu
        275                 280                 285

Gly Leu Ala Tyr Asp Leu Lys Lys Phe Arg Ala Asn Glu Ile Glu Lys
    290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
                325                 330                 335

Asp Tyr Val Glu Gln Ala Lys Asn Gly Arg Gly Leu Val Ala Ile Ala
            340                 345                 350

Gly Val Val His Asp Val Thr Asp Phe Ile Lys Asp His Pro Gly Gly
        355                 360                 365

Lys Ala Met Ile Ser Ser Gly Ile Gly Lys Asp Ala Thr Ala Met Phe
    370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Gly Cys Glu Val Glu Ile Trp
                405                 410                 415

```
Lys Arg Ala Gln Lys Glu Asn Val Glu Tyr Val Arg Asp Gly Ser Gly
            420                 425                 430

Gln Arg Val Ile Arg Ala Gly Glu Gln Pro Thr Lys Ile Pro Glu Pro
            435                 440                 445

Ile Pro Thr Ala Asp Ala Ala
    450                 455

<210> SEQ ID NO 30
<211> LENGTH: 455
<212> TYPE: PRT
<213> ORGANISM: Aspergillus nidulans

<400> SEQUENCE: 30

Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
            20                  25                  30

His Val Asn Trp Leu Asn Val Phe Leu Ile Ile Gly Ile Pro Leu Tyr
            35                  40                  45

Gly Cys Ile Gln Ala Phe Trp Val Pro Leu Gln Leu Lys Thr Ala Ile
    50                  55                  60

Trp Ala Val Ile Tyr Tyr Phe Phe Thr Gly Leu Gly Ile Thr Ala Gly
65              70                  75                  80

Tyr His Arg Leu Trp Ala His Cys Ser Tyr Ser Ala Thr Leu Pro Leu
                85                  90                  95

Arg Ile Trp Leu Ala Ala Val Gly Gly Gly Ala Val Glu Gly Ser Ile
            100                 105                 110

Arg Trp Trp Ala Arg Asp His Arg Ala His His Arg Tyr Thr Asp Thr
        115                 120                 125

Asp Lys Asp Pro Tyr Ser Val Arg Lys Gly Leu Leu Tyr Ser His Leu
    130                 135                 140

Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
                165                 170                 175

Tyr Leu Lys Val Val Phe Thr Met Gly Leu Ala Val Pro Met Leu Val
            180                 185                 190

Ala Gly Leu Gly Trp Gly Asp Trp Leu Gly Gly Phe Val Tyr Ala Gly
        195                 200                 205

Ile Leu Arg Ile Phe Phe Val Gln Gln Ala Thr Phe Cys Val Asn Ser
    210                 215                 220

Leu Ala Leu Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
                245                 250                 255

Asn Phe His His Glu Phe Pro Ser Asp Tyr Arg Asn Ala Ile Glu Trp
            260                 265                 270

His Gln Tyr Asp Pro Thr Lys Trp Ser Ile Trp Ala Trp Lys Gln Leu
        275                 280                 285

Gly Leu Ala Tyr Asp Leu Lys Lys Phe Arg Ala Asn Glu Ile Glu Lys
    290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
```

```
            325                 330                 335
Asp Tyr Val Glu Gln Ala Lys Asn Gly Arg Gly Leu Val Ala Ile Ala
        340                 345                 350

Gly Val Val His Asp Val Thr Asp Phe Ile Lys Asp His Pro Gly Gly
        355                 360                 365

Lys Ala Met Ile Ser Ser Gly Ile Gly Lys Asp Ala Thr Ala Met Phe
        370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Gly Cys Glu Val Glu Ile Trp
                405                 410                 415

Lys Arg Ala Gln Lys Glu Asn Val Glu Tyr Val Arg Asp Gly Ser Gly
                420                 425                 430

Gln Arg Val Ile Arg Ala Gly Glu Gln Pro Thr Lys Ile Pro Glu Pro
            435                 440                 445

Ile Pro Thr Ala Asp Ala Ala
        450                 455

<210> SEQ ID NO 31
<211> LENGTH: 510
<212> TYPE: PRT
<213> ORGANISM: Saccharomyces cerevisiae

<400> SEQUENCE: 31

Met Pro Thr Ser Gly Thr Thr Ile Glu Leu Ile Asp Asp Gln Phe Pro
1               5                   10                  15

Lys Asp Asp Ser Ala Ser Ser Gly Ile Val Asp Glu Val Asp Leu Thr
            20                  25                  30

Glu Ala Asn Ile Leu Ala Thr Gly Leu Asn Lys Lys Ala Pro Arg Ile
        35                  40                  45

Val Asn Gly Phe Gly Ser Leu Met Gly Ser Lys Glu Met Val Ser Val
    50                  55                  60

Glu Phe Asp Lys Lys Gly Asn Glu Lys Lys Ser Asn Leu Asp Arg Leu
65                  70                  75                  80

Leu Glu Lys Asp Asn Gln Glu Lys Glu Ala Lys Thr Lys Ile His
                85                  90                  95

Ile Ser Glu Gln Pro Trp Thr Leu Asn Asn Trp His Gln His Leu Asn
                100                 105                 110

Trp Leu Asn Met Val Leu Val Cys Gly Met Pro Met Ile Gly Trp Tyr
            115                 120                 125

Phe Ala Leu Ser Gly Lys Val Pro Leu His Leu Asn Val Phe Leu Phe
        130                 135                 140

Ser Val Phe Tyr Tyr Ala Val Gly Gly Val Ser Ile Thr Ala Gly Tyr
145                 150                 155                 160

His Arg Leu Trp Ser His Arg Ser Tyr Ser Ala His Trp Pro Leu Arg
                165                 170                 175

Leu Phe Tyr Ala Ile Phe Gly Cys Ala Ser Val Glu Gly Ser Ala Lys
            180                 185                 190

Trp Trp Gly His Ser His Arg Ile His His Arg Tyr Thr Asp Thr Leu
        195                 200                 205

Arg Asp Pro Tyr Asp Ala Arg Arg Gly Leu Trp Tyr Ser His Met Gly
    210                 215                 220

Trp Met Leu Leu Lys Pro Asn Pro Lys Tyr Lys Ala Arg Ala Asp Ile
225                 230                 235                 240
```

```
Thr Asp Met Thr Asp Asp Trp Thr Ile Arg Phe Gln His Arg His Tyr
            245                 250                 255

Ile Leu Leu Met Leu Leu Thr Ala Phe Val Ile Pro Thr Leu Ile Cys
260                 265                 270

Gly Tyr Phe Phe Asn Asp Tyr Met Gly Gly Leu Ile Tyr Ala Gly Phe
            275                 280                 285

Ile Arg Val Phe Val Ile Gln Gln Ala Thr Phe Cys Ile Asn Ser Met
290                 295                 300

Ala His Tyr Ile Gly Thr Gln Pro Phe Asp Arg Arg Thr Pro Arg
305                 310                 315                 320

Asp Asn Trp Ile Thr Ala Ile Val Thr Phe Gly Glu Gly Tyr His Asn
            325                 330                 335

Phe His His Glu Phe Pro Thr Asp Tyr Arg Asn Ala Ile Lys Trp Tyr
            340                 345                 350

Gln Tyr Asp Pro Thr Lys Val Ile Ile Tyr Leu Thr Ser Leu Val Gly
            355                 360                 365

Leu Ala Tyr Asp Leu Lys Lys Phe Ser Gln Asn Ala Ile Glu Glu Ala
            370                 375                 380

Leu Ile Gln Gln Glu Gln Lys Lys Ile Asn Lys Lys Ala Lys Ile
385                 390                 395                 400

Asn Trp Gly Pro Val Leu Thr Asp Leu Pro Met Trp Asp Lys Gln Thr
            405                 410                 415

Phe Leu Ala Lys Ser Lys Glu Asn Lys Gly Leu Val Ile Ile Ser Gly
            420                 425                 430

Ile Val His Asp Val Ser Gly Tyr Ile Ser Glu His Pro Gly Gly Glu
            435                 440                 445

Thr Leu Ile Lys Thr Ala Leu Gly Lys Asp Ala Thr Lys Ala Phe Ser
450                 455                 460

Gly Gly Val Tyr Arg His Ser Asn Ala Ala Gln Asn Val Leu Ala Asp
465                 470                 475                 480

Met Arg Val Ala Val Ile Lys Glu Ser Lys Asn Ser Ala Ile Arg Met
            485                 490                 495

Ala Ser Lys Arg Gly Glu Ile Tyr Glu Thr Gly Lys Phe Phe
            500                 505                 510
```

<210> SEQ ID NO 32
<211> LENGTH: 68
<212> TYPE: PRT
<213> ORGANISM: Artificial Sequence
<220> FEATURE:
<223> OTHER INFORMATION: N-terminal residues 1-68 of AnD9DS

<400> SEQUENCE: 32

```
Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
            20                  25                  30

His Val Asn Trp Leu Asn Val Phe Leu Ile Ile Gly Ile Pro Leu Tyr
            35                  40                  45

Gly Cys Ile Gln Ala Phe Trp Val Pro Leu Gln Leu Lys Thr Ala Ile
        50                  55                  60

Trp Ala Val Ile
65
```

<210> SEQ ID NO 33
<211> LENGTH: 175

```
-continued

<212> TYPE: PRT
<213> ORGANISM: Artificial Sequence
<220> FEATURE:
<223> OTHER INFORMATION: C-terminal residues 281-455 of AnD9DS

<400> SEQUENCE: 33

Ser Ile Trp Ala Trp Lys Gln Leu Gly Leu Ala Tyr Asp Leu Lys Lys
1               5                   10                  15

Phe Arg Ala Asn Glu Ile Glu Lys Gly Arg Val Gln Gln Leu Gln Lys
            20                  25                  30

Lys Leu Asp Arg Lys Arg Ala Thr Leu Asp Trp Gly Thr Pro Leu Asp
        35                  40                  45

Gln Leu Pro Val Met Glu Trp Asp Asp Tyr Val Glu Gln Ala Lys Asn
    50                  55                  60

Gly Arg Gly Leu Val Ala Ile Ala Gly Val Val His Asp Val Thr Asp
65                  70                  75                  80

Phe Ile Lys Asp His Pro Gly Gly Lys Ala Met Ile Ser Ser Gly Ile
                85                  90                  95

Gly Lys Asp Ala Thr Ala Met Phe Asn Gly Gly Val Tyr Tyr His Ser
            100                 105                 110

Asn Ala Ala His Asn Leu Leu Ser Thr Met Arg Val Gly Val Ile Arg
        115                 120                 125

Gly Gly Cys Glu Val Glu Ile Trp Lys Arg Ala Gln Lys Glu Asn Val
    130                 135                 140

Glu Tyr Val Arg Asp Gly Ser Gly Gln Arg Val Ile Arg Ala Gly Glu
145                 150                 155                 160

Gln Pro Thr Lys Ile Pro Glu Pro Ile Pro Thr Ala Asp Ala Ala
                165                 170                 175
```

GENERATION OF TRANSGENIC CANOLA WITH LOW OR NO SATURATED FATTY ACIDS

CROSS-REFERENCE TO RELATED APPLICATIONS

This application is a continuation of co-pending application U.S. patent application Ser. No. 14/578,008, filed Dec. 19, 2014, which is a continuation-in-part of co-pending application U.S. patent application Ser. No. 13/168,742, filed Jun. 24, 2011, which is a continuation-in-part of co-pending application U.S. patent application Ser. No. 11/576,750, which is a national phase entry of PCT International Patent Application No. PCT/US05/36052, filed Oct. 7, 2005, designating the United States of America, and published, in English, as PCT International Publication No. WO 2006/042049 A2 on Apr. 20, 2006. PCT International Patent Application No. PCT/US05/36052 is a continuation of U.S. Provisional Patent Application No. 60/617,532, filed Oct. 8, 2004. The contents of the entirety of each of the foregoing are hereby incorporated in their entireties herein by this reference.

FIELD OF THE INVENTION

Some embodiments generally relate to certain delta-9 desaturase enzymes, nucleic acids encoding these enzymes, and methods of expressing the same in a plant cell. Some embodiments relate to utilizing the activity of certain delta-9 desaturase enzymes to decrease the percent composition of saturated fatty acids in plant materials (e.g., seed) and increasing the percent composition of ω-7 fatty acids. Further embodiments relate to utilizing seed-specific promoters to preferentially express delta-9 desaturase enzymes in seeds. Also disclosed herein are plants and plant materials produced by methods in particular embodiments, and oil produced by those plants which contains less than 3.5% or less than 2.7% saturated fatty acids.

BACKGROUND

Vegetable-derived oils have gradually replaced animal-derived oils and fats as the major source of dietary fat intake. However, saturated fat intake in most industrialized nations has remained at about 15% to 20% of total caloric consumption. In efforts to promote healthier lifestyles, the United States Department of Agriculture (USDA) has recently recommended that saturated fats make up less than 10% of daily caloric intake. To facilitate consumer awareness, current labeling guidelines issued by the USDA now require total saturated fatty acid levels be less than 1.0 g per 14 g serving to receive the "low-sat" label and less than 0.5 g per 14 g serving to receive the "no-sat" label. This means that the saturated fatty acid content of plant oils needs to be less than 7% and 3.5% to receive the "low-sat" or "no-sat" label, respectively. Since issuance of these guidelines, there has been a surge in consumer demand for "low-sat" and "no-sat" oils. To date, this demand has been met principally with canola oil, and to a much lesser degree with sunflower and safflower oils.

While unsaturated fats (monounsaturated and polyunsaturated) are beneficial (especially when consumed in moderation), saturated and trans fats are not. Saturated fat and trans fat raise undesirable LDL cholesterol levels in the blood. Dietary cholesterol also raises LDL cholesterol and may contribute to heart disease even without raising LDL. Therefore, it is advisable to choose foods low in saturated fat, trans fat, and cholesterol as part of a healthful diet.

The characteristics of oils, whether of plant or animal origin, are determined predominately by the number of carbon and hydrogen atoms in the oil molecule, as well as the number and position of double bonds comprised in the fatty acid chain. Most oils derived from plants are composed of varying amounts of palmitic (16:0), stearic (18:0), oleic (18:1), linoleic (18:2) and linolenic (18:3) fatty acids. Conventionally, palmitic and stearic acids are designated as "saturated," because their carbon chains are saturated with hydrogen atoms, and hence have no double bonds; they contain the maximal number of hydrogen atoms possible. However, oleic, linoleic, and linolenic acids are 18-carbon fatty acid chains having one, two, and three double bonds, respectively, therein. Oleic acid is typically considered a monounsaturated fatty acid, whereas linoleic and linolenic are considered to be polyunsaturated fatty acids. The U.S.D.A. definition of "no sat" oil products, meaning those having less than 3.5% saturated fatty acid content, is calculated as the combined saturated fatty acid content by weight (as compared to the total amount of fatty acids).

Canola oil has the lowest level of saturated fatty acids of all vegetable oils. "Canola" refers to rapeseed (*Brassica*) which has an erucic acid (C22:1) content of at most 2% by weight, based on the total fatty acid content of a seed (preferably at most 0.5% by weight, and most preferably essentially 0% by weight), and which produces, after crushing, an air-dried meal containing less than 30 μmol/g of glucosinolates in defatted (oil-free) meal. These types of rapeseed are distinguished by their edibility in comparison to more traditional varieties of the species.

It is postulated that, in oilseeds, fatty acid synthesis occurs primarily in the plastid. The major product of fatty acid synthesis is palmitate (16:0), which appears to be efficiently elongated to stearate (18:0). While still in the plastid, the saturated fatty acids may then be desaturated by an enzyme known as acyl-ACP delta-9 desaturase, to introduce one or more carbon-carbon double bonds. Specifically, stearate may be rapidly desaturated by a plastidial delta-9 desaturase enzyme to yield oleate (18:1). In fact, palmitate may also be desaturated to palmitoleate (16:1) by the plastidial delta-9 desaturase, but this fatty acid appears in only trace quantities (0-0.2%) in most vegetable oils. Thus, the major products of fatty acid synthesis in the plastid are palmitate, stearate, and oleate. In most oils, oleate is the major fatty acid synthesized, as the saturated fatty acids are present in much lower proportions.

Newly-synthesized fatty acids are exported from the plastid to the cytoplasm. Subsequent desaturation of plant fatty acids in the cytoplasm appears to be limited to oleate, which may be desaturated to linoleate (18:2) and linolenate (18:3) by microsomal desaturases acting on oleoyl or linoleoyl substrates esterified to phosphatidyl choline (PC). In addition, depending on the plant, oleate may be further modified by elongation (to 20:1, 22:1, and/or 24:1), or by the addition of functional groups. These fatty acids, along with the saturated fatty acids, palmitate and stearate, are then assembled into triglycerides in endoreticular membranes.

The plant acyl-ACP delta-9 desaturase enzyme is soluble. It is located in the plastid stroma, and uses newly-synthesized fatty acids esterified to ACP, predominantly stearyl-ACP, as substrates. This is in contrast to the other delta-9 desaturase enzymes, which are located in the endoplasmic reticular membrane (ER, or microsomal), use fatty acids esterified to Co-A as substrates, and desaturate both the saturated fatty acids, palmitate and stearate. U.S. Pat. Nos. 5,723,595 and 6,706,950 relate to a plant desaturase.

The yeast delta-9 desaturase gene has been isolated from *Saccharomyces cerevisiae*, cloned, and sequenced. Stukey et al. (1989) *J. Biol. Chem.* 264:16537-44; Stukey et al. (1990) *J. Biol. Chem.* 265:20144-9. This yeast gene has been introduced into tobacco leaf tissue (Polashcok et al. (1991) *FASEB J.* 5:A1157; Polashok et al. (1992) *Plant Physiol.* 100:894-901), and was apparently expressed in this tissue. Further, this yeast gene was expressed in tomato. See Wang et al. (1996) *J. Agric. Food Chem.* 44:3399-402; and Wang et al. (2001) *Phytochemistry* 58:227-32. While some increases in certain unsaturated fatty acids, and some decreases in certain saturated fatty acids, were reported for both tobacco and tomato using this yeast delta-9 desaturase gene, tobacco and tomato are clearly not oil crops. This yeast gene was also introduced into *Brassica napus*. U.S. Pat. No. 5,777,201.

A different fungal acyl-CoA delta-9 desaturase from *Aspergillus nidulans* has been introduced into canola, thereby achieving reduced saturated fatty acid levels in seed oil. U.S. Patent Application Publication US 2008/0260933 A1. The *A. nidulans* acyl-CoA delta-9 desaturase provided greater depletion of stearate (61-90%) than the more abundant palmitate fatty acids (36-49%) in the seed oil.

BRIEF SUMMARY OF THE INVENTION

Disclosed herein are novel fungal delta-9 desaturase enzymes; nucleic acids comprising at least one nucleotide sequence encoding such a desaturase; and plants, plant materials (e.g., seed), plant parts, and plant commodity products comprising either of the foregoing. Aspects of some embodiments are exemplified by fungal delta-9 desaturase enzymes isolated from *Magnaporthe grisea, Leptosphaeria nodorum*, and *Helicoverpa zea*. Some examples include native and synthetic delta-9 desaturases that have a substrate preference for palmitic acid or stearic acid.

Some embodiments comprise an isolated nucleic acid molecule encoding a delta-9 desaturase enzyme comprising an amino acid sequence being at least 80% identical to a sequence selected from the group consisting of SEQ ID NO:1, SEQ ID NO:26, SEQ ID NO:27, SEQ ID NO:28 SEQ ID NO:29, SEQ ID NO:30, SEQ ID NO:31, SEQ ID NO:32, and SEQ ID NO:33. In particular examples, the nucleic acid molecule comprises a sequence being at least 60% identical to a sequence selected from the group consisting of SEQ ID NO:2, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. These and further embodiments may include an isolated delta-9 desaturase polypeptide comprising an amino acid sequence being at least 80% identical to a sequence selected from the group consisting of SEQ ID NO:1, SEQ ID NO:26, SEQ ID NO:27, SEQ ID NO:28 SEQ ID NO:29, SEQ ID NO:30, SEQ ID NO:31, SEQ ID NO:32, and SEQ ID NO:33.

Also disclosed are methods of expressing at least one of the aforementioned nucleic acids and/or polypeptides in a plant cell. Particular embodiments take advantage of a delta-9 desaturase enzyme's activity, such that the percent composition of saturated fatty acids may be decreased in a plant, plant material (e.g., seed), and/or plant part comprising the plant cell, and/or a plant commodity product produced from any of the foregoing. In certain embodiments, ω-7 fatty acids may concomitantly be increased in the plant, plant material, plant part, and/or plant commodity product. Further embodiments take advantage of seed-specific expression to further lower the level of saturated fatty acids in seed oil.

Some embodiments include a method for decreasing the amount of saturated fatty acids in a plant, plant material, plant part, and/or plant commodity product, the method comprising transforming a plant cell with a nucleic acid molecule encoding a delta-9 desaturase polypeptide of the invention, such that the amount of saturated fatty acids in the cell is decreased. Some embodiments include a method for creating a genetically engineered plant that comprises decreased amounts of saturated fatty acids in the plant compared to a wild-type plant of the same species. Such a method may comprise transforming a plant material (or plant cell) with a nucleic acid molecule encoding one or more delta-9 desaturase polypeptides, or one or more copies of a delta-9 desaturase polypeptide of the invention, and culturing the transformed plant material (or plant cell) to obtain a plant. In particular examples, a plant cell and/or plant material from an *Arabidopsis* sp. may be transformed with a nucleic acid molecule encoding a delta-9 desaturase polypeptide of the invention. In other particular examples, the two or more copies of the delta-9 desaturase gene may be transformed, where each delta-9 desaturase gene is controlled by a different promoter. In other particular examples, the two or more promoters are seed specific promoters.

The foregoing and other features will become more apparent from the following detailed description of several embodiments, which proceeds with reference to the accompanying figures.

SEQUENCE LISTING

Figure 1:
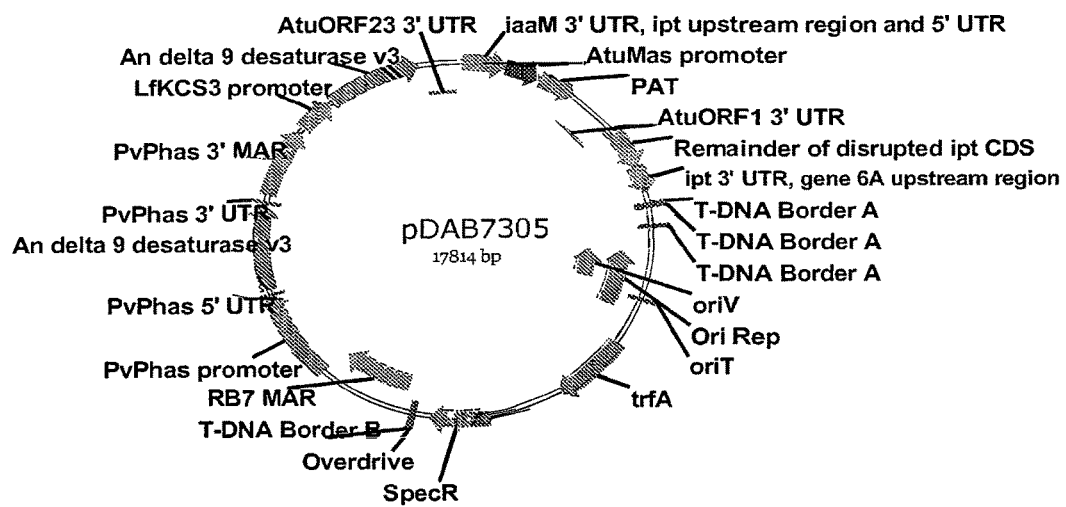
FIG. 1 shows a plasmid map of pDAB7305.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood to be included by any reference to the displayed strand. In the accompanying sequence listing:

SEQ ID NO:1 shows the amino acid sequence of *Aspergillus nidulans* acyl-CoA delta-9 desaturase protein (referred to in some places as AnD9DS).

SEQ ID NO:2 shows the nucleic acid sequence of the v3 of the *Aspergillus nidulas* acyl-CoA delta-9 desaturase gene (referred to in some places as AnD9DS).

SEQ ID NO:3 shows the nucleic acid sequence the first plant transcription unit (PTU) of pDAB7305.

SEQ ID NO:4 shows the nucleic acid sequence of the second PTU of pDAB7305.

SEQ ID NO:5 shows the nucleic acid sequence of the third PTU of pDAB7305.

SEQ ID NOs:6-11 show the sequence of primers and probes that may be useful in some embodiments.

SEQ ID NO:12 is an exemplary fragment of a *M. grisea* acyl-CoA delta-9 desaturase gene (referred to in some places as MgD9DS) that was amplified by PCR SEQ ID NO:13 is an exemplary intronless MgD9DS clone SEQ ID NO:14 shows an exemplary nucleic acid sequence encoding a first *Leptosphaeria nodorum* acyl-CoA delta-9 desaturase, referred to in some places as LnD9DS-1

SEQ ID NO:15 shows an exemplary nucleic acid sequence encoding a second exemplary *L. nodorum* acyl-CoA delta-9 desaturase, referred to in some places as LnD9DS-2

SEQ ID NO:16 shows a coding region from an exemplary native delta-9 desaturase gene from *M. grisea* (labeled as MgD9DS v1).

SEQ ID NO:17 shows a coding region from an exemplary native delta-9 desaturase gene from *Helicoverpa zea* (labeled as HzD9DS v1).

SEQ ID NO:18 shows a coding region from an exemplary native delta-9 desaturase (LnD9DS-2 v1) gene from *L. nodorum*.

SEQ ID NO:19 shows the sequence of an exemplary canola-optimized delta-9 desaturase gene from *M. grisea* (MgD9DS v2).

SEQ ID NO:20 shows the sequence of an exemplary canola-optimized delta-9 desaturase gene from *H. zea* (HzD9DS v2).

SEQ ID NO:21 shows the sequence of an exemplary canola-optimized delta-9 desaturase gene from *L. nodorum* (LnD9DS-2 v2).

SEQ ID NO:22 shows the sequence of a further exemplary canola-optimized delta-9 desaturase gene from *L. nodorum* (LnD9DS-2 v3).

SEQ ID NO:23 shows the sequence of a further exemplary canola-optimized delta-9 desaturase gene from *H. zea* (HzD9DS v3).

SEQ ID NO:24 shows an exemplary nucleic acid sequence encoding an *Aspergillus nidulans* delta-9 desaturase, referred to in some places as AnD9DS v2.

SEQ ID NO:25 shows a second exemplary nucleic acid sequence encoding an *A. nidulans* delta-9 desaturase, referred to in some places as AnD9DS v3.

SEQ ID NO:26 shows the amino acid sequence of an exemplary native delta-9 desaturase from *M. grisea* (MgD9DS).

SEQ ID NO:27 shows the amino acid sequence of an exemplary native delta-9 desaturase from *H. zea* (HzD9DS).

SEQ ID NO:28 shows the amino acid sequence of an exemplary native delta-9 desaturase from *L. nodorum* (LnD9DS-2).

SEQ ID NO:29 shows the amino acid sequence encoded by nucleic acids as exemplified by SEQ ID NOs:24-25 (AnD9DS).

SEQ ID NO:30 shows the amino acid sequence of another exemplary AnD9DS desaturase.

SEQ ID NO:31 shows the amino acid sequence of an exemplary native delta-9 desaturase (ScOLE1) from *Saccharomyces cerevisiae*.

SEQ ID NO:32 shows the N-terminal 68 residues (1-68) of an exemplary AnD9DS desaturase.

SEQ ID NO:33 shows the C-terminal 175 residues (281-455) of an exemplary AnD9DS desaturase.

DETAILED DESCRIPTION

I. Overview of Several Embodiments

We previously introduced a fungal acyl-CoA delta-9 desaturase from *Aspergillus nidulans* into canola, thereby achieving reduced saturated fatty acid levels in seed oil. U.S. Patent Application Publication US 2008/0260933 A1. The *A. nidulans* delta-9 desaturase provided greater depletion of stearate (61-90%) than the more abundant palmitate fatty acids (36-49%) in the seed oil. It was discovered that providing multiple copies of the *A. nidulans* delta-9 desaturase was able to reduce the saturated fatty acid levels in canola below 3.5%.

Disclosed herein are nucleic acid molecules encoding a delta-9 desaturase polypeptide comprising a nucleotide sequence being at least 60% identical to a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. In some embodiments, the nucleic acid molecule may further comprise a gene regulatory element operably linked to the delta-9 desaturase polypeptide-encoding sequence. In particular embodiments, a gene regulatory element may be a phaseolin promoter, a phaseolin 5' untranslated region, a phaseolin 3' untranslated region ("UTR"), an *Agrobacterium tumefaciens* ORF1 3' untranslated region, a Cassava vein Mosaic Virus promoter, a *Nicotiana tabacum* RB7 Matrix Attachment Region, a T-strand border sequence, a LfKCS3 promoter, and FAE 1 promoter.

In some embodiments, there may be several copies of the nucleic acid molecules encoding a delta-9 desaturase polypeptide, and each may be under the regulatory control of a different set of regulatory elements. More specifically, the gene regulatory elements may be phaseolin promoter and phaseolin 5' UTR, and *Lesquerella fenderi* LfKCS3 promoter, such that two copies of the AND9DS is present, one copy controlled by the phaseolin promoter and 5' UTR, and a second copy controlled by the LfKCS3 promoter. In other embodiments, the several copies of the nucleic acid encoding a delta-9 desaturase polypeptide (or multiple delta-9 destaurase polypeptides) may be under the control of other regulatory elements, including the *Saccharomyces cerevisiae* delta-9 desaturase promoter, the delta-9 desaturase 3' UTR/terminator, the ole1 gene promoter, the *Phaseolus vulgaris* phaseolin 3' untranslated region, the *Phaseolus vulgaris* phaseolin matrix attachment region, the *Agrobacterium tumefaciens* Mannopine Synthase promoter, the *Agrobacterium tumefaciens* ORF23 3' untranslated region, the Cassava vein Mosaic Virus Promoter, the *Agrobacterium tumefaciens* ORF1 3' untranslated region, the *Nicotiana tabacum* RB7 Matrix Attachment Region, Overdrive, T-stand border sequences, the LfKCS3 promoter, FAE 1 promoter, a Myc tag, and a hemagglutin tag.

Also disclosed are delta-9 desaturase polypeptides comprising an amino acid sequence being at least 80% identical to a sequence selected from the group consisting of SEQ ID NO:1 as well as nucleic acid molecules encoding such delta-9 desaturase polypeptides, such as SEQ ID NO:2.

In some embodiments, nucleic acid molecules and delta-9 desaturase polypeptides may be expressed in a plant material, cell, tissue, or whole plant, to decrease the amount of saturated fatty acids in the plant material, cells, tissues, or whole plants, relative to the amount observed in a wild-type plant of the same species. Alternative embodiments of the invention include methods for decreasing the amount of saturated fatty acids in the plant material, cell, tissue, or whole plant. Such methods may comprise transforming a plant material, cell, tissue, or whole plant with at least one of the aforementioned nucleic acid molecules, such that the amount of saturated fatty acids in the plant material, cell, tissue, or whole plant is decreased. Particular embodiments include methods for preferentially decreasing palmitic and/or stearic fatty acids in a plant material, cell, tissue, or whole plant.

Methods disclosed herein may be performed, for example, on plants, or plant materials derived from plants (e.g., plants of the genus *Arabidopsis*, or canola). A particular embodiment is drawn to methods for creating or regenerating a genetically engineered plant comprising decreased amounts of saturated fatty acids in the plant compared to a wild-type plant of the same species, the method comprising transforming a plant cell or material with at least one of the aforementioned nucleic acid molecules; and culturing the transformed plant material to obtain a plant. Plants, plant materials, plant cells, and seeds obtained by any of the aforementioned methods are also disclosed.

II. Abbreviations $x:y\Delta^z$ fatty acid containing x carbons and y double bonds in position z counting from the carboxyl end
ACP acyl carrier protein
CoA coenzyme A
FA fatty acids
FAS fatty acid synthase
FAME fatty acid methyl ester
KASII β-ketoacyl-ACP synthase II
MUFA monounsaturated fatty acid
PUFA polyunsaturated fatty acid
WT wild type III. Terms Fatty acid: As used herein, the term "fatty acid" refers to long chain aliphatic acids (alkanoic acids) of varying chain lengths, for example, from about C12 to C22, although both longer and shorter chain-length acids are known. The structure of a fatty acid is represented by the notation, $x:y\Delta^z$, where "x" is the total number of carbon (C) atoms in the particular fatty acid, and "y" is the number of double bonds in the carbon chain in the position "z," as counted from the carboxyl end of the acid.

Metabolic pathway: The term, "metabolic pathway," refers to a series of chemical reactions occurring within a cell, catalyzed by enzymes, to achieve either the formation of a metabolic product, or the initiation of another metabolic pathway. A metabolic pathway may involve several or many steps, and may compete with a different metabolic pathway for specific reaction substrates. Similarly, the product of one metabolic pathway may be a substrate for yet another metabolic pathway.

Metabolic engineering: For the purposes of the present invention, "metabolic engineering" refers to the rational design of strategies to alter one or more metabolic pathways in a cell, such that the step-by-step modification of an initial substance into a product having the exact chemical structure desired is achieved within the overall scheme of the total metabolic pathways operative in the cell.

Desaturase: As used herein, the term "desaturase" refers to a polypeptide that can desaturate (i.e., introduce a double bond) in one or more fatty acids to produce a fatty acid or precursor of interest. A plant-soluble fatty acid desaturase enzyme may introduce a double bond regiospecifically into a saturated acyl-ACP substrate. Acyl-CoA desaturases introduce a double bond regiospecifically into a saturated fatty acyl-CoA substrate. The reaction involves activation of molecular oxygen by a two-electron reduced diiron center coordinated by a four-helix bundle that forms the core of the desaturase architecture. Of particular interest in some embodiments are acyl-CoA delta-9 desaturases.

The delta-9-18:0$^1$-ACP desaturase is required by all plants for the maintenance of membrane fluidity. While this enzyme primarily desaturates stearoyl-ACP, it is also active to a minor extent with palmitoyl-ACP.

Progeny plant: For the purposes of the present invention, "progeny plant," refers to any plant, or plant material obtained therefrom, that may be obtained by plant breeding methods. Plant breeding methods are well-known in the art, and include natural breeding, artificial breeding, selective breeding involving DNA molecular marker analysis, transgenics, and commercial breeding.

Plant material: As used herein, the term "plant material" refers to any cell or tissue obtained from a plant.

Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide, or a modified form of either type of nucleotide. A "nucleic acid molecule" as used herein is synonymous with "nucleic acid" and "polynucleotide." The term includes single- and double-stranded forms of DNA. A nucleic acid molecule can include either or both naturally occurring and modified nucleotides linked together by naturally occurring and/or non-naturally occurring nucleotide linkages.

Nucleic acid molecules can be modified chemically or biochemically, or can contain non-natural or derivatized nucleotide bases, as will be readily appreciated by those of ordinary skill in the art. Such modification include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, peptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

Operably linked: A first nucleic acid sequence is operably linked with a second nucleic acid sequence when the first nucleic acid sequence is in a functional relationship with the second nucleic acid sequence. For instance, a promoter is operably linked to a coding sequence if the promoter affects the transcription or expression of the coding sequence.

When recombinantly produced, operably linked nucleic acid sequences are generally contiguous and, where necessary to join two protein-coding regions, in the same reading frame. However, nucleic acids need not be contiguous to be operably linked.

Regulatory element: As used herein, the term "regulatory element" refers to a nucleic acid molecule having gene regulatory activity; i.e., one that has the ability to affect the transcription or translation of an operably-linked transcribable nucleic acid molecule. Regulatory elements such as promoters, leaders, introns, and transcription termination regions are non-coding nucleic acid molecules having gene regulatory activity which play an integral part in the overall expression of genes in living cells. Isolated regulatory elements that function in plants are therefore useful for modifying plant phenotypes through the techniques of molecular engineering. By "regulatory element," it is intended a series of nucleotides that determines if, when, and at what level a particular gene is expressed. The regulatory DNA sequences specifically interact with regulatory proteins or other proteins.

As used herein, the term "gene regulatory activity" refers to a nucleic acid molecule capable of affecting transcription or translation of an operably linked nucleic acid molecule. An isolated nucleic acid molecule having gene regulatory activity may provide temporal or spatial expression or modulate levels and rates of expression of the operably linked nucleic acid molecule. An isolated nucleic acid molecule having gene regulatory activity may comprise a promoter, intron, leader, or 3' transcriptional termination region.

Promoters: As used herein, the term "promoter" refers to a nucleic acid molecule that is involved in recognition and binding of RNA polymerase II or other proteins such as transcription factors (trans-acting protein factors that regulate transcription) to initiate transcription of an operably linked gene. Promoters may themselves contain sub-elements such as cis-elements or enhancer domains that effect the transcription of operably linked genes. A "plant promoter" is a native or non-native promoter that is functional in plant cells. A plant promoter can be used as a 5' regulatory element for modulating expression of an operably linked gene or genes. Plant promoters may be defined by their temporal, spatial, or developmental expression pattern. The nucleic acid molecules described herein may comprise nucleic acid sequences comprising promoters.

Sequence identity: The term "sequence identity" or "identity," as used herein in the context of two nucleic acid or polypeptide sequences, may refer to the residues in the two sequences that are the same when aligned for maximum correspondence over a specified comparison window.

When percentage of sequence identity is used in reference to proteins, it is recognized that residue positions which are not identical often differ by conservative amino acid substitutions, where amino acid residues are substituted for other amino acid residues with similar chemical properties (e.g., charge, hydrophobicity, or steric effects), and therefore do not change the functional properties of the molecule.

Therefore, when sequences differ by conservative substitutions, the percent sequence identity may be adjusted upwards to correct for the conservative nature of the substitution at the site of the non-identical residue. Sequences that differ by such conservative substitutions are said to have "sequence similarity" or "similarity." Techniques for making this adjustment are well known to those of ordinary skill in the art. Typically, such techniques involve scoring a conservative substitution as a partial, rather than a full, mismatch, thereby increasing the percentage sequence identity. For example, where an identical amino acid is given a score between 0 and 1, and a non-conservative substitution is given a score of 0, a conservative substitution is given a score between 0 and 1. The scoring of conservative substitutions may be calculated, for example, as implemented in the program PC/GENE (Intelligenetics, Mountain View, Calif.).

As used herein, the term "percentage of sequence identity" may refer to the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Analogous position in an amino acid sequence: Nucleic acid and amino acid sequences may be aligned by the methods described in the following paragraphs. When aligned, a position in one sequence is in "an analogous position" with a position in the aligned sequence if the positions are identical within the consensus sequence.

Methods for aligning sequences for comparison are well-known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-44, 1988; Higgins and Sharp, *CABIOS* 5:151-3, 1989; Corpet et al., *Nucleic Acids Research* 16:10881-10890, 1988; Huang, et al., *Computer Applications in the Biosciences* 8:155-65, 1992; Pearson et al., *Methods in Molecular Biology* 24:307-31, 1994; Tatiana et al., *FEMS Microbiol. Lett.*, 174:247-50, 1990; Altschul et al., *J. Mol. Biol.* 215:403-10, 1990 (detailed consideration of sequence-alignment methods and homology calculations).

The National Center for Biotechnology Information (NCBI) Basic Local Alignment Search Tool (BLAST) is available on the Internet (at blast.ncbi.nlm.nih.gov/Blast.cgi), for use in connection with sequence-analysis programs, for example, blastp and blastn. A description of how to determine sequence identity using this program is available on the Internet through NCBI at blast.ncbi.nlm.nih.gov/Blast.cgi?CMD=Web&PAGE_TYPE=BlastDocs.

For comparisons of amino acid sequences, the "Blast 2 sequences" function of the BLAST program (bl2seq) is employed using the default parameters. Specific parameters may be adjusted within the discretion of one of skill in the art, to for example, provide a penalty for a mismatch or reward for a match.

Transformed: As used herein, the term "transformed" refers to a cell, tissue, organ, or organism into which has been introduced a foreign nucleic acid molecule, such as a construct. The introduced nucleic acid molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in, for example, a cross and exhibiting an altered phenotype resulting from the presence of a foreign nucleic acid molecule.

IV. Metabolic Engineering Approaches to Decreasing Saturated Fatty Acids in a Host Cell, Tissue, or Organism A. Overview An embodiment of the invention includes introducing delta-9 desaturases with specific acyl-CoA preferences (for example, for palmitic or stearic acid) in plant seeds. The specific acyl-CoA preference of the delta-9 desaturase enables targeting of certain specific saturated fatty acid pools (e.g., palmitate for conversion to monounsaturated products). Acyl-CoA delta-9 desaturases were selected for lowering the saturated fatty acid content in plants as they are not normally produced in plant systems to any appreciable extent.

B. Polypeptides

Polypeptides according to some embodiments of the present invention comprise an amino acid sequence showing increasing percentage identities when aligned with a sequence selected from the group consisting of SEQ ID NO:1, SEQ ID NO:26, SEQ ID NO:27, SEQ ID NO:28 SEQ ID NO:29, SEQ ID NO:30, SEQ ID NO:31, SEQ ID NO:32, and SEQ ID NO:33. Specific amino acid sequences within these and other embodiments may comprise sequences having, for example, at least about 70%, about 75%, about 80%, 81%, 82%, 83%, 84%, 85%, 86%, 87%, 88%, 89%, 90%, 91%, 92%, 93%, 94%, 95% 96%, 97%, 98%, 99%, or 100% identity with the aforementioned sequences. In many embodiments, the amino acid sequence having the aforementioned sequence identity when aligned with the aforementioned sequences encode a peptide with enzymatic delta-9-18:0-ACP desaturase activity, or part of a such a peptide.

C. Nucleic Acids

Some embodiments include nucleic acid molecules encoding a polypeptide described above. For example, nucleic acid sequences in some embodiments show increasing percentage identities when aligned with a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. Specific nucleic acid sequences within these and other embodiments may comprise sequences having, for example, at least about 60%, about 65%, about 70%, about 75%, about 80%, 81%, 82%, 83%, 84%, 85%, 86%, 87%, 88%, 89%, 90%, 91%, 92%, 93%, 94%, 95% 96%, 97%, 98%, 99%, or 100% identity with a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. It is understood by those of ordinary skill in the art that nucleic acid molecules may be modified without substantially changing the amino acid sequence of an encoded polypeptide, for example, by introducing permissible nucleotide substitutions according to codon degeneracy.

In some embodiments, nucleic acid molecules of the present invention comprise a gene regulatory element (e.g., a promoter). Promoters may be selected on the basis of the cell type into which the vector construct will be inserted. Promoters which function in bacteria, yeast, and plants are well-known in the art. The promoters may also be selected on the basis of their regulatory features. Examples of such features include enhancement of transcriptional activity, inducibility, tissue-specificity, and developmental stage-specificity. In plants, promoters that are inducible, of viral or synthetic origin, constitutively active, temporally regulated, and spatially regulated have been described. See, e.g., Poszkowski et al. (1989) *EMBO J.* 3:2719; Odell et al. (1985) *Nature* 313:810; and Chau et al. (1989) *Science* 244:174-81).

Useful inducible promoters include, for example, promoters induced by salicylic acid or polyacrylic acids induced by application of safeners (substituted benzenesulfonamide herbicides), heat-shock promoters, a nitrate-inducible promoter derived from the spinach nitrate reductase transcribable nucleic acid molecule sequence, hormone-inducible promoters, and light-inducible promoters associated with the small subunit of RuBP carboxylase and LHCP families.

Examples of useful tissue-specific, developmentally-regulated promoters include the β-conglycinin 7Sα promoter and seed-specific promoters. Plant functional promoters useful for preferential expression in seed plastid include those from proteins involved in fatty acid biosynthesis in oilseeds and from plant storage proteins. Examples of such promoters include the 5' regulatory regions from such transcribable nucleic acid molecule sequences as phaseolin, napin, zein, soybean trypsin inhibitor, ACP, stearoyl-ACP desaturase, and oleosin. Another exemplary tissue-specific promoter is the lectin promoter, which is specific for seed tissue.

More specifically, promoters may include the *Phaseolus vulgaris* Phaseolin promoter, (alone or in conjunction with the *Phaseolus vulgaris* Phaseolin 3' untranslated region and the *Phaseolus vulgaris* Phaseolin 3' Matrix Attachment Region), the *Lesquerella fendleri* KCS3 promoter, or the *Agrobacterium tumefaciens* Mannopine Synthase promoter.

Other useful promoters include the nopaline synthase, mannopine synthase, and octopine synthase promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus 35S promoter; the light-inducible promoter from the small subunit of ribulose-1,5-bisphosphate carboxylase (ssRUBISCO); the EIF-4A promoter from tobacco (Mandel et al. (1995) Plant Mol. Biol. 29:995-1004); corn sucrose synthetase; corn alcohol dehydrogenase I; corn light harvesting complex; corn heat shock protein; the chitinase promoter from *Arabidopsis*; the LTP (Lipid Transfer Protein) promoters; petunia chalcone isomerase; bean glycine rich protein 1; potato patatin; the ubiquitin promoter; and the actin promoter. Useful promoters are preferably seed-selective, tissue selective, or inducible. Seed-specific regulation is discussed in, for example, EP 0 255 378.

To obtain higher expression of a heterologous gene(s), it may be preferred to reengineer the gene(s) so that it is more efficiently expressed in the expression host cell (e.g., a plant cell, for example, canola, rice, tobacco, maize, cotton, and soybean). Therefore, an optional additional step in the design of a gene encoding a delta-9 desaturase for plant expression (i.e., in addition to the provision of one or more gene regulatory elements) is reengineering of a heterologous gene protein coding region for optimal expression. Particular embodiments include redesigned genes that have been optimized to increase the expression level (i.e. produce more protein) in a transgenic canola plant cell or *Arabidopsis* plant cell than in a canola plant cell or *Arabidopsis* plant cell transformed with the naturally-occurring heterologous gene sequence.

Due to the plasticity afforded by the redundancy/degeneracy of the genetic code (i.e., some amino acids are specified by more than one codon), evolution of the genomes in different organisms or classes of organisms has resulted in differential usage of synonymous codons. This "codon bias" is reflected in the mean base composition of protein coding regions. For example, organisms having genomes with relatively low G+C contents utilize more codons having A or T in the third position of synonymous codons, whereas those having higher G+C contents utilize more codons having G or C in the third position. Further, it is thought that the presence of "minor" codons within an mRNA may reduce the absolute translation rate of that mRNA, especially when the relative abundance of the charged tRNA corresponding to the minor codon is low. An extension of this reasoning is that the diminution of translation rate by individual minor codons would be at least additive for multiple minor codons. Therefore, mRNAs having high relative contents of minor codons in a particular expression host would have correspondingly low translation rates. This rate may be reflected by correspondingly low levels of the encoded protein.

In engineering optimized genes encoding a delta-9 desaturase for expression in canola or *Arabidopsis* (or other plants, such as rice, tobacco, maize, cotton or soybean), it is helpful if the codon bias of the prospective host plant(s) has been determined. Multiple publicly-available DNA sequence databases exist wherein one may find information about the codon distribution of plant genomes or the protein coding regions of various plant genes.

The codon bias is the statistical distribution of codons that the expression host (e.g., a plant such as canola or *Arabidopsis*) uses for coding the amino acids of its proteins. The codon bias can be calculated as the frequency at which a single codon is used relative to the codons for all amino acids. Alternatively, the codon bias may be calculated as the frequency at which a single codon is used to encode a particular amino acid, relative to all the other codons for that amino acid (synonymous codons).

In designing optimized coding regions for plant expression of delta-9 desaturase genes, the primary ("first choice") codons preferred by the plant should be determined, as well as the second, third, fourth etc. choices of preferred codons when multiple choices exist. A new DNA sequence can then be designed which encodes the amino sequence of the delta-9 desaturase gene, wherein the new DNA sequence differs from the native DNA sequence (encoding the desaturase) by the substitution of expression host-preferred (first preferred, second preferred, third preferred, or fourth preferred, etc.) codons to specify the amino acid at each position within the amino acid sequence. The new sequence is then analyzed for restriction enzyme sites that might have been created by the modifications. The identified putative restriction sites are further modified by replacing these codons with a next-preferred codon to remove the restriction site. Other sites in the sequence which may affect transcription or translation of heterologous sequence are exon:intron junctions (5' or 3'), poly-A addition signals, and/or RNA polymerase termination signals. The sequence may be further analyzed and modified to reduce the frequency of TA or CG doublets. In addition to these doublets, sequence blocks that have more than about six G or C nucleotides that are the same may also adversely affect transcription or translation of the sequence. Therefore, these blocks are advantageously modified by replacing the codons of first or second choice, etc. with the next-preferred codon of choice.

The method described above enables one skilled in the art to modify gene(s) that are foreign to a particular plant so that the genes are optimally expressed in plants. The method is further illustrated in PCT application WO 97/13402. Thus, optimized synthetic genes that are functionally equivalent to desaturases/genes of some embodiments may be used to transform hosts, including plants. Additional guidance regarding the production of synthetic genes can be found in, for example, U.S. Pat. No. 5,380,831.

Once a plant-optimized DNA sequence has been designed on paper or in silico, actual DNA molecules can be synthesized in the laboratory to correspond in sequence precisely to the designed sequence. Such synthetic DNA molecules may be cloned and otherwise manipulated exactly as if they were derived from natural or native sources.

D. Methods for Genetic Transformation of Plant Material

Some embodiments are directed to a method of producing a transformed cell that comprises one or more nucleic acid molecule(s) comprising a nucleic acid sequence at least 60% identical to a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. Such nucleic acid molecules may also comprise, for example, non-coding regulatory elements, such as promoters. Other sequences may also be introduced into the cell along with the non-coding regulatory elements and transcribable nucleic acid molecule sequences. These other sequences may include 3' transcriptional terminators, 3' poly-adenylation signals, other untranslated sequences, transit or targeting sequences, selectable markers, enhancers, and operators.

A method of transformation generally comprises the steps of selecting a suitable host cell, transforming the host cell with a recombinant vector, and obtaining the transformed host cell. Technology for introduction of DNA into cells is well-known to those of skill in the art. These methods can generally be classified into five categories: (1) chemical methods (Graham and Van der Eb (1973) *Virology* 54(2): 536-9; Zatloukal et al. (1992) *Ann. N.Y. Acad. Sci.* 660:136-53); (2) physical methods such as microinjection (Capechi (1980) *Cell* 22(2):479-88), electroporation (Wong and Neumann (1982) *Biochim. Biophys. Res. Commun.* 107(2):584-7; Fromm et al. (1985) *Proc. Natl. Acad. Sci. USA* 82(17): 5824-8; U.S. Pat. No. 5,384,253), and particle acceleration (Johnston and Tang (1994) *Methods Cell Biol.* 43(A):353-65; Fynan et al. (1993) *Proc. Natl. Acad. Sci. USA* 90(24): 11478-82; (3) viral vectors (Clapp (1993) *Clin. Perinatol.* 20(1):155-68; Lu et al. (1993) *J. Exp. Med.* 178(6):2089-96; Eglitis and Anderson (1988) *Biotechniques* 6(7):608-14); (4) receptor-mediated mechanisms (Curiel et al. (1992) *Hum. Gen. Ther.* 3(2):147-54; Wagner et al. (1992) *Proc. Natl. Acad. Sci. USA* 89(13):6099-103); and (5) bacterial-mediated mechanisms, such as with *Agrobacterium*. Alternatively, nucleic acids may be directly introduced into pollen by directly injecting a plant's reproductive organs. Zhou et al. (1983) *Methods in Enzymology* 101:433; Hess (1987) *Intern. Rev. Cytol.* 107:367; Luo et al. (1988) *Plant Mot. Biol. Reporter* 6:165; Pena et al. (1987) *Nature* 325:274. Other transformation methods include, for example, protoplast transformation as illustrated in U.S. Pat. No. 5,508, 184. Nucleic acid molecules may also be injected into immature embryos. Neuhaus et al. (1987) *Theor. Appl. Genet.* 75:30.

The most commonly used methods for transformation of plant cells are: the *Agrobacterium*-mediated DNA transfer process (Fraley et al. (1983) *Proc. Natl. Acad. Sci. USA* 80:4803) (as illustrated in U.S. Pat. Nos. 5,824,877; 5,591,616; 5,981,840; and 6,384,301) and the biolistics or microprojectile bombardment-mediated process (i.e., the gene gun) (such as described in U.S. Pat. Nos. 5,550,318; 5,538,880; 6,160,208; 6,399,861; and 6,403,865). Typically, nuclear transformation is desired, but where it is desirable to specifically transform plastids, such as chloroplasts or amyloplasts, plant plastids may be transformed utilizing a microprojectile-mediated delivery of the desired nucleic acid molecule in certain plant species, such as for example, *Arabidopsis*, tobacco, potato, and *Brassica* species.

*Agrobacterium*-mediated transformation is achieved through the use of a genetically engineered soil bacterium belonging to the genus *Agrobacterium*. Several *Agrobacterium* species mediate the transfer of a specific DNA known as "T-DNA," which can be genetically engineered to carry any desired piece of DNA into many plant species. The major events marking the process of T-DNA mediated pathogensis are: induction of virulence genes, and processing and transfer of T-DNA. This process is the subject of many reviews. See, e.g., Ream (1989) *Ann. Rev. Phytopathol.* 27:583-618; Howard and Citovsky (1990) *Bioassays* 12:103-8; Kado (1991) *Crit. Rev. Plant Sci.* 10:1-32; Zambryski (1992) *Annual Rev. Plant Physiol. Plant Mol. Biol.* 43:465-90; Gelvin (1993) in *Transgenic Plants*, Kung and Wu eds., Academic Press, San Diego, Calif., pp. 49-87; Binns and Howitz (1994) In *Bacterical Pathogenesis of Plants and Animals*, Dang, ed., Berlin: Springer Verlag., pp. 119-38; Hooykaas and Beijersbergen (1994) *Ann. Rev. Phytopathol.* 32:157-79; Lessl and Lanka (1994) *Cell* 77:321-4; and Zupan and Zambryski (1995) *Annual Rev. Phytopathol.* 27:583-618.

To select or score for transformed plant cells regardless of transformation methodology, the DNA introduced into the cell may contain a gene that functions in a regenerable plant tissue to produce a compound that confers upon the plant tissue resistance to an otherwise toxic compound. Genes of interest for use as a selectable, screenable, or scorable marker include, but are not limited to, β-glucuronidase (GUS), green fluorescent protein (GFP), luciferase, and antibiotic or herbicide tolerance genes. Examples of antibiotic resistance genes include genes conferring resistance to the penicillins, kanamycin (and neomycin, G418, bleomycin); methotrexate (and trimethoprim); chloramphenicol; and tetracycline. For example, glyphosate resistance may be conferred by a herbicide resistance gene. Della-Cioppa et al. (1987) *Bio/Technology* 5:579-84. Other selection devices can also be implemented, including for example and without limitation, tolerance to phosphinothricin, bialaphos, and positive selection mechanisms (Joersbro et al. (1998) *Mol. Breed.* 4:111-7), and are considered within the scope of embodiments of the present invention.

The transformed cells, identified by selection or screening and cultured in an appropriate medium that supports regeneration, may then be allowed to mature into plants.

The presently disclosed methods may be used with any transformable plant cell or tissue. Transformable cells and tissues, as used herein, includes but is not limited to those cells or tissues that are capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

The regeneration, development, and cultivation of plants from transformed plant protoplast or explants are known in the art. Weissbach and Weissbach (1988) *Methods for Plant Molecular Biology*, (Eds.) Academic Press, Inc., San Diego, Calif.; Horsch et al. (1985) *Science* 227:1229-31. This regeneration and growth process typically includes the steps of selecting transformed cells and culturing those cells through the usual stages of embryonic development through the rooted plantlet stage. Transgenic embryos and seeds are similarly regenerated. In this method, transformants are generally cultured in the presence of a selective media which selects for the successfully transformed cells and induces the regeneration of plant shoots. Fraley et al. (1993) *Proc. Natl. Acad. Sci. USA* 80:4803. These shoots are typically obtained within two to four months. The resulting transgenic rooted shoots are thereafter planted in an appropriate plant growth medium such as soil. Cells that survive the exposure to a selective agent, or cells that have been scored positive in a screening assay, may be cultured in media that supports regeneration of plants. The shoots may then be transferred to an appropriate root-inducing medium containing the selective agent and an antibiotic to prevent bacterial growth. Many of the shoots will develop roots. These are then transplanted to soil or other media to allow the continued development of roots. The method, as outlined above, will generally vary depending on the particular plant strain employed, and particulars of the methodology are therefore within the discretion of one of skill in the art.

The regenerated transgenic plants may be self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transgenic plant may pass along the transformed nucleic acid sequence to its progeny. The transgenic plant is preferably homozygous for the transformed nucleic acid sequence and transmits that sequence to all of its offspring upon, and as a result of, sexual reproduction. Progeny may be grown from seeds produced by the transgenic plant. These additional plants may then be self-pollinated to generate a true breeding line of plants.

The progeny from these plants may be evaluated, among other things, for gene expression. The gene expression may be detected by several common methods such as western blotting, northern blotting, immunoprecipitation, and ELISA (Enzyme-Linked ImmunoSorbent Assay). The transformed plants may also be analyzed for the presence of the introduced DNA and the expression level and/or fatty acid profile conferred by the nucleic acid molecules and amino acid molecules of the present invention. Those of skill in the art are aware of the numerous methods available for the analysis of transformed plants. For example, methods for plant analysis include, but are not limited to, Southern blots or northern blots, PCR-based approaches, biochemical assays, phenotypic screening methods, field evaluations, and immunodiagnostic assays.

Methods for specifically transforming dicots are well-known to those skilled in the art. Transformation and plant regeneration using these methods have been described for a number of crops including, but not limited to, members of the genus *Arabidopsis*, cotton (*Gossypium hirsutum*), soybean (*Glycine max*), peanut (*Arachis hypogaea*), and members of the genus *Brassica*. Methods for transforming dicots, primarily by use of *Agrobacterium tumefaciens*, and obtaining transgenic plants have been published for cotton (U.S. Pat. Nos. 5,004,863; 5,159,135; 5,518,908); soybean (U.S. Pat. Nos. 5,569,834; 5,416,011; McCabe et al. (1988) *Biotechnology* 6:923; Christou et al. (1988) *Plant Physiol.* 87:671-4); *Brassica* (U.S. Pat. No. 5,463,174); peanut (Cheng et al. (1996) *Plant Cell Rep.* 15:653-7; McKently et al. (1995) *Plant Cell Rep.* 14:699-703); papaya; and pea (Grant et al. (1995) *Plant Cell Rep.* 15:254-8).

Methods for transforming monocots are also well-known in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum sp*); tall fescue (*Festuca arundinacea*); turfgrass species (e.g., *Agrostis stolonifera*, *Poa pratensis*, *Stenotaphrum secundatum*); wheat (*Triticum aestivum*); and alfalfa (*Medicago sativa*). It is apparent to those of skill in the art that a number of transformation methodologies can be used and modified for production of stable transgenic plants for any number of target crops of interest.

Any plant may be chosen for use in the presently disclosed methods. Preferred plants for modification according to the present invention include, for example and without limitation, oilseed plants, *Arabidopsis thaliana*, borage (*Borago* spp.), canola (*Brassica* spp.), castor (*Ricinus communis*), cocoa bean (*Theobroma cacao*), corn (*Zea mays*), cotton (*Gossypium* spp), *Crambe* spp., *Cuphea* spp., flax (*Linum* spp.), *Lesquerella* and *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), and rye (*Secale* spp.) or other members of the *Gramineae*.

It is apparent to those of skill in the art that a number of transformation methodologies can be used and modified for production of stable transgenic plants from any number of target crops of interest.

E. Transgenic Seeds

In some embodiments, a transgenic seed may comprise a delta-9 desaturase polypeptide comprising an amino acid sequence being at least 80% identical to a sequence selected from the group consisting of SEQ ID NO:1, SEQ ID NO:26, SEQ ID NO:27, SEQ ID NO:28 SEQ ID NO:29, SEQ ID NO:30, SEQ ID NO:31, SEQ ID NO:32, and SEQ ID NO:33. In these and other embodiments, the transgenic seed may comprise a nucleic acid sequence being at least 60% identical to a sequence selected from the group consisting of SEQ ID NO:2, SEQ ID NO:3, SEQ ID NO:4, SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25. In certain embodiments, a transgenic seed may exhibit decreased levels of saturated fatty acids (for example, palmitic fatty acids and/or stearic fatty acids). The seeds may be harvested from a fertile transgenic plant, and may be used to grow progeny generations of transformed plants, including hybrid plant lines comprising at least one nucleic acid sequence as set forth above, and optionally at least one additional gene or nucleic acid construct of interest.

Each document, patent, and reference cited herein is herein incorporated by its entirety.

The following examples are provided to illustrate certain particular features and/or embodiments. These examples should not be construed to limit the invention to the particular features or embodiments described.

EXAMPLES

Example 1: Construct Design of pDAB7305

The *Aspergillus nidulans* Δ-9 Desaturase (AnD9DS) enzyme was previously disclosed in U.S. Patent App. No. 2008/0260933, herein incorporated by reference in its entirety, and is presented herein as SEQ ID NO:1. A polynucleotide sequence (SEQ ID NO:2) comprising the AnD9DS v3 coding sequence was synthesized and incorporated into plasmid construct pDAB7305 (FIG. 1) for *Agrobacterium*-mediated plant transformation. The resulting construct contained three plant transcription units (also described and used interchangeably as a gene expression cassette). The first plant transcription unit (PTU) (SEQ ID NO:3) was comprised of the RB7 Matrix Attachment Region (RB7 MAR; International Patent App. No. WO9727207), *Phaseolus vulgaris* Phaseolin promoter (Pv Phas promoter; U.S. Pat. No. 5,504,200), AnD9DS coding sequence (An delta 9 desaturase v3), *Phaseolus vulgaris* Phaseolin 3' untranslated region (Pv Phas 3' UTR; U.S. Pat. No. 5,504,200), and the *Phaseolus vulgaris* Phaseolin 3' Matrix Attachment Region (Pv Phas 3' MAR; U.S. Pat. No. 5,504,200). The second PTU (SEQ ID NO:4) was comprised of the *Lesquerella fendleri* KCS3 promoter (LfKCS3 promoter; U.S. Pat. No. 7,253,337), AnD9DS coding sequence (An delta 9 desaturase v3), and *Agrobacterium tumefaciens* ORF 23 3' untranslated region (AtuORF23 3'UTR; U.S. Pat. No. 5,428,147). The third PTU (SEQ ID NO:5) was comprised of *Agrobacterium tumefaciens* Mannopine Synthase promoter (AtuMas promoter; Barker, R. F., Idler, K. B., Thompson, D. V., Kemp, J. D., (1983), a polynucleotide sequence of the T-DNA region from the *Agrobacterium tumefaciens* octopine Ti plasmid pTi15955, *Plant Molecular Biology*, 2(6), 335-50), phosphinothricin acetyl transferase gene (PAT; Wohlleben et al., (1988) *Gene*, 70: 25-37), and *Agrobacterium tumefaciens* ORF 1 3' untranslated region (AtuORF1 3' UTR; Huang et al., (1990) *J. Bacteriol.*, 172: 1814-1822). The construct was confirmed via restriction enzyme digestion and sequencing. Finally, the construct was transformed into *Agrobacterium tumefaciens* and stored as a glycerol stock.

Example 2: *Agrobacterium*-Mediated Transformation of Canola (*Brassica napus*) Hypocotyls *Agrobacterium* Preparation The *Agrobacterium* strain containing the pDAB7305 binary plasmid was streaked out on YEP media (Bacto Peptone™ 20.0 gm/L and Yeast Extract 10.0 gm/L) plates containing streptomycin (100 mg/ml) and spectinomycin (50 mg/mL) and incubated for 2 days at 28° C. The propagated *Agrobacterium* strain containing the pDAB7305 binary plasmid was scraped from the 2-day streak plate using a sterile inoculation loop. The scraped *Agrobacterium* strain containing the pDAB7305 binary plasmid was then inoculated into 150 mL modified YEP liquid with streptomycin (100 mg/ml) and spectinomycin (50 mg/ml) into sterile 500 mL baffled flask(s) and shaken at 200 rpm at 28° C. The cultures were centrifuged and resuspended in M-medium (LS salts, 3% glucose, modified B5 vitamins, 1 µM kinetin, 1 µM 2,4-D, pH 5.8) and diluted to the appropriate density (50 Klett Units as measured using a spectrophotometer) prior to transformation of canola hypocotyls.

Canola Transformation

Seed germination: Canola seeds (var. NEXERA 710™) were surface-sterilized in 10% Clorox™ for 10 minutes and rinsed three times with sterile distilled water (seeds are contained in steel strainers during this process). Seeds were planted for germination on ½ MS Canola medium (½ MS, 2% sucrose, 0.8% agar) contained in Phytatrays™ (25 seeds per Phytatray™) and placed in a Percival™ growth chamber with growth regime set at 25° C., photoperiod of 16 hours light and 8 hours dark for 5 days of germination.

Pre-treatment: On day 5, hypocotyl segments of about 3 mm in length were aseptically excised, the remaining root and shoot sections were discarded (drying of hypocotyl segments was prevented by immersing the hypocotyls segments into 10 mL of sterile milliQ™ water during the excision process). Hypocotyl segments were placed horizontally on sterile filter paper on callus induction medium, MSK1D1 (MS, 1 mg/L kinetin, 1 mg/L 2,4-D, 3.0% sucrose, 0.7% phytagar) for 3 days pre-treatment in a Percival™ growth chamber with growth regime set at 22-23° C., and a photoperiod of 16 hours light, 8 hours dark.

Co-cultivation with *Agrobacterium*: The day before *Agrobacterium* co-cultivation, flasks of YEP medium containing the appropriate antibiotics, were inoculated with the *Agrobacterium* strain containing the pDAB7305 binary plasmid. Hypocotyl segments were transferred from filter paper callus induction medium, MSK1D1 to an empty 100×25 mm Petri™ dishes containing 10 mL of liquid M-medium to prevent the hypocotyl segments from drying. A spatula was used at this stage to scoop the segments and transfer the segments to new medium. The liquid M-medium was removed with a pipette and 40 mL of *Agrobacterium* suspension was added to the Petri™ dish (500 segments with 40 mL of *Agrobacterium* solution). The hypocotyl segments were treated for 30 minutes with periodic swirling of the Petri™ dish so that the hypocotyl segments remained immersed in the *Agrobacterium* solution. At the end of the treatment period, the *Agrobacterium* solution was pipetted into a waste beaker; autoclaved and discarded (the *Agrobacterium* solution was completely removed to prevent *Agrobacterium* overgrowth). The treated hypocotyls were transferred with forceps back to the original plates containing MSK1D1 media overlaid with filter paper (care was taken to ensure that the segments did not dry). The transformed hypocotyl segments and non-transformed control hypocotyl segments were returned to the Percival™ growth chamber under reduced light intensity (by covering the plates with aluminum foil), and the treated hypocotyl segments were co-cultivated with *Agrobacterium* for 3 days.

Callus induction on selection medium: After 3 days of co-cultivation, the hypocotyl segments were individually transferred with forceps onto callus induction medium, MSK1D1H1 (MS, 1 mg/L kinetin, 1 mg/L 2,4-D, 0.5 gm/L MES, 5 mg/L AgNO$_3$, 300 mg/L Timentin™, 200 mg/L carbenicillin, 1 mg/L Herbiace™, 3% sucrose, 0.7% phytagar) with growth regime set at 22-26° C. The hypocotyl segments were anchored on the medium but were not deeply embedded into the medium.

Selection and shoot regeneration: After 7 days on callus induction medium, the callusing hypocotyl segments were transferred to Shoot Regeneration Medium 1 with selection, MSB3Z1H1 (MS, 3 mg/L BAP, 1 mg/L zeatin, 0.5 gm/L MES, 5 mg/L AgNO$_3$, 300 mg/L Timentin™, 200 mg/L carbenicillin, 1 mg/L Herbiace™, 3% sucrose, 0.7% phytagar). After 14 days, the hypocotyl segments which had developed shoots were transferred to Regeneration Medium 2 with increased selection, MSB3Z1H3 (MS, 3 mg/L BAP, 1 mg/L Zeatin, 0.5 gm/L IVIES, 5 mg/L AgNO$_3$, 300 mg/l Timentin™, 200 mg/L carbenicillin, 3 mg/L Herbiace™, 3% sucrose, 0.7% phytagar) with growth regime set at 22-26° C.

Shoot elongation: After 14 days, the hypocotyl segments that had developed shoots were transferred from Regeneration Medium 2 to shoot elongation medium, MSMESH5 (MS, 300 mg/L Timentin™, 5 mg/l Herbiace™, 2% sucrose, 0.7% TC Agar) with growth regime set at 22-26° C. Shoots that were already elongated were isolated from the hypocotyl segments and transferred to MSMESH5. After 14 days the remaining shoots which had not elongated in the first round of culturing on shoot elongation medium were transferred to fresh shoot elongation medium, MSMESH5. At this stage all remaining hypocotyl segments which did not produce shoots were discarded.

Root induction: After 14 days of culturing on the shoot elongation medium, the isolated shoots were transferred to MSMEST medium (MS, 0.5 g/L IVIES, 300 mg/L Timentin™, 2% sucrose, 0.7% TC Agar) for root induction at 22-26° C. Any shoots which did not produce roots after incubation in the first transfer to MSMEST medium were transferred for a second or third round of incubation on MSMEST medium until the shoots developed roots.

PCR analysis: Transformed canola hypocotyl segments which regenerated into shoots comprising roots were further analyzed via a PCR molecular confirmation assay. Leaf tissue was obtained from the green shoots and tested via the PCR for the presence of the pat selectable marker gene. Any chlorotic shoots were discarded and not subjected to the PCR analysis. Samples that were identified as positive for presence of the pat selectable marker gene were kept and cultured on the MSMEST medium to continue development and elongation of the shoots and roots. The samples that were identified as not containing the pat selectable marker gene negative according to the PCR analysis were discarded.

The transformed canola plants comprising shoots and roots that were PCR-positive for the presence of the pat selectable marker gene were transplanted into soil in a greenhouse. After establishment of the canola plants within soil, the canola plants were further analyzed to quantitate the copy number of the pat gene expression cassette via an Invader™ quantitative PCR assay and Southern blotting. Transgenic $T_0$ canola plants which were confirmed to contain at least one copy of the pat gene expression cassette were advanced for further analysis of the seed fatty acid profile. The seeds obtained from theses transgenic $T_0$ canola plants, i.e., $T_1$ canola seeds, were analyzed via a FAME analysis method to identify events which comprise a reduction in total saturated fatty acids (total saturated fatty acid content was determined by summing all of the saturated fatty acids, including short and long chain fatty acids) as compared to control plants.

Example 3: FAME Analysis of $T_1$ Canola Seeds Obtained from Transgenic pDAB7305 Canola Plants Segregating $T_1$ canola seeds were analyzed via a FAME analysis method to identify $T_0$ canola events which produced $T_1$ canola seeds comprising a reduction in total saturated fatty acids (C14:0, C16:0, C18:0, C20:0, C22:0, C24:0) as compared to seeds obtained from control plants grown in the same conditions. The sum of all Total Saturated Fatty Acids (TSFA) were quantitated and compared to a negative control plant. The FAME analysis was completed using the protocol described below on a single $T_1$ canola seed. A total of 24 single $T_1$ canola seed from each individual canola $T_0$ event were assayed and the TSFA results from each single were quantitated.

Single canola seed samples were homogenized in heptane containing triheptadecanoin (Nu-Chek prep) as a triacylglycerol internal standard, using steel ball mill. Prior to homogenization, a solution of 0.25 M of freshly prepared sodium methoxide (Sigma-Aldrich, St. Louis, Mo.) in methanol was added. Extraction was conducted at 40° C. with constant shaking. Endogenous fatty acid recoveries were normalized by the recovery of the methylated surrogate C17 fatty acid. Extraction of FAMEs (fatty acid methyl esters) was repeated three times and the heptane layers were pooled prior to analysis. The resulting FAMEs were analyzed by GC-FID using a capillary column BPX 70 from SGE (15 m×0.25 mm×0.25 µm). Each FAME was identified by retention time and quantified by the injection of a rapeseed oil reference mix from Matreya LLC (Pleasant Gap, Pa.) as a calibration standard with addition of appropriate long chain fatty acids (Nu-Chek Prep, Elysian Minn.).

The bulk seed analysis consisted of 50 mg aliquot (10 to 15 seeds combined) and followed the same protocol described above with a slight modification. In order to drive the reaction of derivatization to completeness, the oil was first extracted three times with heptane. Then an aliquot of the combined oil extract, corresponding to 1 seed, was derivatized in FAMEs as described in the single seed protocol above. The completeness of the reaction was verified by checking for the presence of endogenous FAMEs in a fourth extraction/derivatization.

Three transgenic canola events (Event 2182[12]-138.001, Event 2182[12]-125.001, and Event 2182[12]-156.001) were identified and selected for advancement to the $T_1$ generation based on the FAME results which indicated a significant reduction in TSFA as compared to control canola plants. Two additional categories of plant fatty acid content were assayed. These categories included the Mono Unsaturated Fatty Acid (MUFA: C16:1, C18:1 and C20:1) and Poly Unsaturated Fatty Acid (PUFA: C18:2 and C18:3) concentrations, are listed to show the effect of lowering TSFA in $T_1$ seed. (Table 1).

The mean TSFA of the transgenic canola events is reduced significantly as compared to the NEXERA 710™ non-transformed control plants. Concomitant to the reduction of TSFA an increase in MUFA content (C18:1 and C16:1) was observed. The increase in MUFA content is the direct result from the over-expression of the AnD9DS introducing a double bond at the $9^{th}$ carbon (Δ9) from the carboxylic function of saturated fatty acid. Interestingly, the PUFA content did not increase with the accumulation of MUFA substrate of phosphoglycerolipid desaturase FAD2 synthesizing C18:2.

Figure 3:
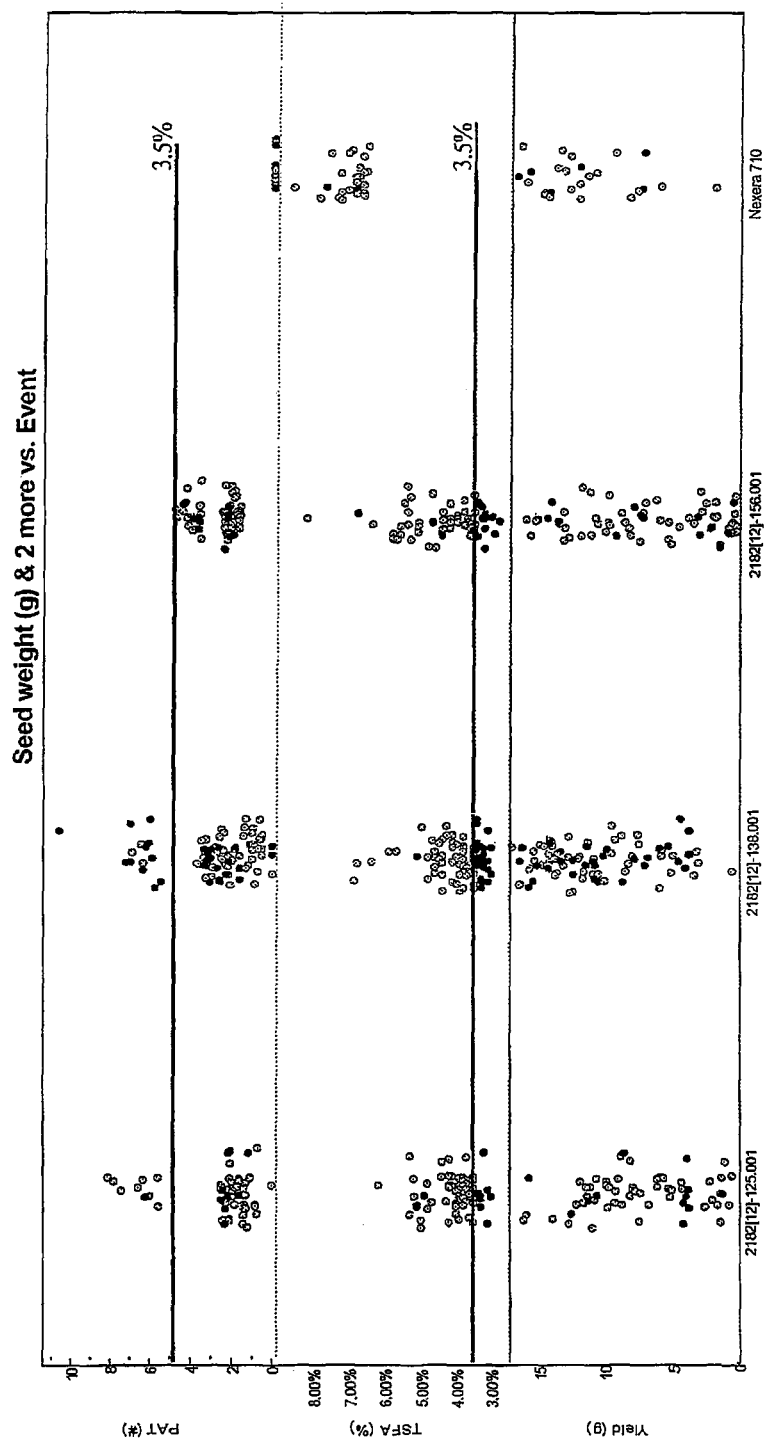
FIG. 3 shows the distribution of TSFA in $T_2$ seed population from three selected transgenic events as compared to the negative control NEXERA 710™ canola plants. Dark dots represent seed progeny with a TSFA lower than 3.5% (dark line). As indicated in the graph, the plants with a TSFA lower than 3.5% produced varying amounts of yield and possessed from 2 to 10 copies numbers of the pat transgene that is contained on the same T-strand integrant as the AnD9DS transgene.

$T_1$ canola plant events were grown in a greenhouse and self-fertilized to fix the introgressed transgene in progeny plants. Invader™ quantitative PCR assays were completed on multiple $T_1$ canola plants from each transgenic event. These results indicated that the $T_1$ canola plants obtained from each of the three events contained about 2 or 3 copies of the pDAB7305 T-strand integration (FIG. 3 top panel). A specific determination of copy number was unobtainable, as the pDAB7305 T-strand integrant segregated at varying copy numbers across the three events. The $T_1$ canola plant events were grown in the greenhouse to maturity and self-fertilized. The resulting $T_2$ canola seed was harvested for fatty acid profile analysis via FAME assay.

Figure 2:
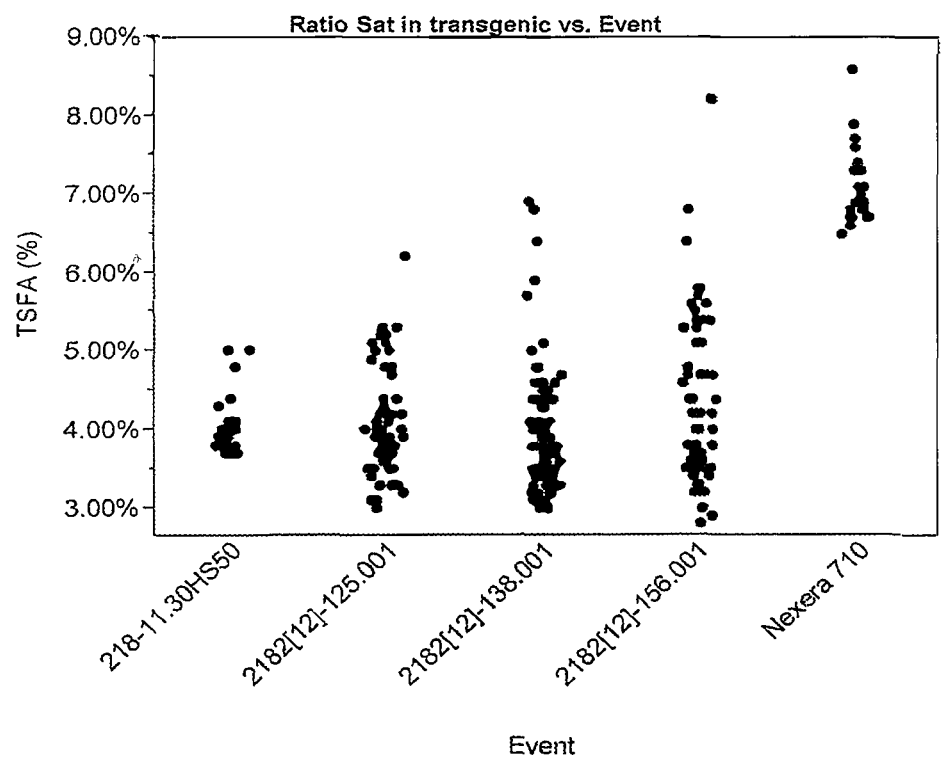
FIG. 2 illustrates the distribution of TSFA (%) in bulk $T_2$ seed from segregating $T_1$ canola plants compared to NEXERA 710™ canola control plants and the positive control plants comprised of the 218-11.30HL transgenic canola plants.

Example 4: FAME Analysis of $T_2$ Canola Seeds Obtained from Transgenic pDAB7305 Canola Plants Bulked $T_2$ canola seeds were analyzed via the previously described FAME analysis method to identify $T_1$ canola plant lines which comprised a reduction in total saturated fatty acids as compared to control plants (NEXERA 710™). (FIG. 2). The yield of each plant was recorded as gram of seed per plant. The yield results were compared to the yield of a transgenic positive control event, 218-11.30 (also described herein as 218-11.30HS50 or 218-11.30HL) containing a stably integrated *Aspergillus nidulans* delta-9 desaturase transgene (See, WO 2006/042049) that was grown alongside the transgenic plants of the subject disclosure. Both the 218-11.30 plants and the transgenic canola plants of the subject disclosure express a similar transgene. However, the construct used in the transformation of the 2182[12]-125.Sx001, 2182[12]-138.Sx001 and 2182[12]-156.Sx00 canola plants in the subject disclosure is different, as it contains a second PTU comprised of a *Lesquerella fendleri* KCS3 promoter driving expression of a AnD9DS

TABLE 1

Summary composition of single $T_1$ seed TSFA, MUFA and PUFA accumulations obtained from three transgenic canola events as compared to several NEXERA 710 ™ non-transformed control plants.

| Event | N* | TSFA (%) | | | MUFA (%) | | | PUFA (%) | | |
|---|---|---|---|---|---|---|---|---|---|---|
| | | Mean | Min | Max | Mean | Min | Max | Mean | Min | Max |
| 2182[12]-125.001 | 23 | 3.16 | 2.30 | 4.30 | 82.74 | 74.00 | 90.20 | 14.09 | 6.50 | 22.20 |
| 2182[12]-138.001 | 24 | 3.40 | 2.70 | 4.70 | 84.10 | 80.40 | 88.90 | 12.50 | 8.00 | 16.30 |
| 2182[12]-156.001 | 23 | 3.49 | 2.80 | 5.00 | 87.30 | 83.00 | 90.70 | 9.23 | 6.00 | 12.50 |
| NEXERA 710.1.16 | 24 | 6.96 | 6.10 | 8.00 | 80.23 | 76.90 | 82.40 | 12.82 | 10.50 | 16.20 |
| NEXERA 710.1.22 | 24 | 6.94 | 5.90 | 8.40 | 79.91 | 77.40 | 82.60 | 13.15 | 10.60 | 16.40 |
| NEXERA 710.1.29 | 24 | 7.06 | 6.10 | 8.50 | 77.33 | 73.20 | 81.70 | 15.64 | 11.50 | 19.40 |
| NEXERA 710.1.5_ | 24 | 6.99 | 6.20 | 7.80 | 82.71 | 78.50 | 84.40 | 10.28 | 8.20 | 13.90 |

N* indicates the number of individual $T_1$ seed analyzed for each plant progeny.

coding sequence, and flanked by the *Agrobacterium tumefaciens* ORF 23 3' untranslated region.

The TSFA (%) of the transgenic plants of the subject disclosure were quantitated and compared to the TSFA (%) obtained from the positive control, 218-11.30HL transgenic canola plants and the negative control, NEXERA 710™ plants. A small number of transgenic plants of the subject disclosure were identified to contain higher levels of TSFA, at levels similar to the negative control NEXERA 710™ plants. These plants are sibling nulls which resulted from segregation of the transgenes during self-fertilization, and do not contain any actively expressing copies of the transgenes of the subject disclosure. These results confirmed that the total saturated fatty acid content of the bulked $T_2$ canola seed was reduced below 3.5% in identified $T_1$ canola plant.

The $T_2$ canola lines were further analyzed to determine which canola lines contained low copy numbers of the pDAB7305 T-strand integrant and produced the high $T_2$ seed yield. (FIG. 3).

Individual canola plants of the subject disclosure were selected which contained less than 3.5% TSFA, produced more than 10 g of yield, and contained the lowest T-strand copy number. Based on these three criteria (levels of TSFA below 3.5%, high seed yield, and low copy number) seven canola plants were selected and advanced for further characterization of the TSFA profile. Copy number was determined from one plant per T1 line, using an Invader Assay. Table 2. These $T_2$ canola plant lines were transferred to the greenhouse, grown to maturity and self-fertilized. The $T_2$ canola plant lines were further analyzed molecularly and the $T_3$ seed was harvested for fatty acid profile analysis via FAME assay.

TABLE 2

The $T_2$ canola lines which were selected based on highest yield (seed weight), lowest PAT copy number (T1 plants) and lowest TSFA are listed.

| Event | Plant Line | Seed Weight (g) | PAT (Copy Number) | TSFA (%) |
|---|---|---|---|---|
| 2182[12]-138.001 | 2182[12]-138.Sx001.sSx085 | 16.37 | 2.6 | 3.03 |
| | 2182[12]-138.Sx001.Sx090 | 16.58 | 2.2 | 3.11 |
| | 2182[12]-138.Sx001.Sx094 | 12.47 | 2.3 | 3.02 |
| | 2182[12]-138.Sx001.Sx029 | 18 | 3.0 | 3.31 |
| | 2182[12]-138.Sx001.Sx084 | 15.59 | 3.1 | 3.08 |
| 2182[12]-125.001 | 2182[12]-125.Sx001.Sx014 | 11.26 | 2.5 | 3.27 |
| 2182[12]-156.001 | 2182[12]-156.Sx001.Sx049 | 14.44 | 2.3 | 3.28 |

Example 5: Molecular Confirmation of $T_2$ Canola Lines

Selected $T_2$ canola events which contained the pat gene expression cassette (and the closely linked AnD9DS gene expression cassettes) were characterized for their molecular integration pattern using quantitative PCR and Southern blot analysis.

AnD9DS Integration Confirmation Via Hydrolysis Probe Assay

The presence of the AnD9DS gene expression cassette was confirmed via hydrolysis probe assays. Isolated $T_2$ canola plants were initially screened via a hydrolysis probe assay, analogous to TAQMAN™, to confirm the presence of the pat transgenes. The data generated from these studies was used to determine the transgene copy number and used to select transgenic canola events for back crossing and advancement to subsequent generations.

Tissue samples were collected in 96-well plates, tissue maceration was performed with a KLECO™ tissue pulverizer and stainless steel beads (Hoover Precision Products, Cumming, Ga.), in Qiagen RLT™ buffer. Following tissue maceration, the genomic DNA was isolated in high-throughput format using the Biosprint 96™ Plant kit (Qiagen, Germantown, Md.) according to the manufacturer's suggested protocol. Genomic DNA was quantified by Quant-IT Pico Green DNA Assay Kit™ (Molecular Probes, Invitrogen, Carlsbad, Calif.). Quantified genomic DNA was adjusted to around 2 ng/µL for the hydrolysis probe assay using a BIOROBOT3000™ automated liquid handler (Qiagen, Germantown, Md.). Transgene copy number determination by hydrolysis probe assay, analogous to TAQMAN® assay, was performed by real-time PCR using the LIGHTCYCLER®480 system (Roche Applied Science, Indianapolis, Ind.). Assays were designed for pat and an internal reference gene HMG1 (Weng et al. (2005). J. AOAC Int. 88(2):577-84) using the LIGHTCYCLER® Probe Design Software 2.0. For amplification, LIGHTCYCLER®480 Probes Master mix (Roche Applied Science, Indianapolis, Ind.) was prepared at 1× final concentration in a 10 µL volume multiplex reaction containing 0.4 µM of each primer for AnD9DS and pat and 0.2 µM of each probe (Table 3). A two-step amplification reaction was performed with an extension at 60° C. for 40 seconds with fluorescence acquisition. All samples were run and the averaged Cycle threshold (Ct) values were used for analysis of each sample. Analysis of real time PCR data was performed using LIGHTCYCLER® software release 1.5 using the relative quant module and is based on the ΔΔCt method. Controls included a sample of genomic DNA from a single copy calibrator and known two copy check that were included in each run. Table 4 lists the results of the hydrolysis probe assays. Copy number was determined from N plants per T1 line (and averaged, giving the value in Table 4), using an qPCR Assay.

TABLE 3

Primer and probe sequences used for hydrolysis probe assay of pat and internal reference (HMG1).

| Gene Detected | Forward Primer | Reverse Primer | Probe | Label |
|---|---|---|---|---|
| PAT v5 | SEQ ID NO: 6 acaagagtggattgatgatctagagaggt | SEQ ID NO: 7 ctttgatgcctatgtgacacgtaaacagt | SEQ ID NO: 8 ccagcgtaagcaataccagccacaacacc | FAM |

TABLE 3-continued

Primer and probe sequences used for hydrolysis probe assay of pat and internal reference (HMG1).

| Gene Detected | Forward Primer | Reverse Primer | Probe | Label |
|---|---|---|---|---|
| HMG1 | SEQ ID NO: 9 cctctctaccaccgtctcacatg | SEQ ID NO: 10 gatctggccggactgtttca | SEQ ID NO: 11 cgctcctcagctaccacctaacca | HEX |

TABLE 4

Copy amount results for the AnD9DS events (T2 plants) as determined using the hydrolysis probe assay.

| | | PAT gene | | |
|---|---|---|---|---|
| Event/Line | N | mean | SD | CV (%) |
| 218-11.30(HL) | 12 | 3.61 | 0.28 | 7.82 |
| 2182[12]-125.Sx001.Sx014 | 35 | 5.93 | 0.98 | 16.48 |
| 2182[12]-138.Sx001.Sx085 | 34 | 9.40 | 1.03 | 11.00 |
| 2182[12]-138.Sx001.Sx090 | 33 | 7.69 | 0.35 | 4.54 |
| 2182[12]-138.Sx001.Sx094 | 35 | 9.98 | 0.79 | 7.93 |
| 2182[12]-156.Sx001.Sx049 | 33 | 4.35 | 0.48 | 11.12 |

The results of the hydrolysis probe assay identified two lines (2182[12]-138.Sx001. Sx094 and 2182[12]-138.SX001.Sx090) which had a combination of relative standard deviation (shown in Table 4 as SD) and coefficient of variation (shown in Table 4 as CV %) that were comparable to the positive control plants (218-11.30(HL)). The 218-11.30(HL) control plants were previously identified to contain two fixed copies of the AnD9DS gene insertion (WO 2006042049). By comparing the selected canola lines (2182[12]-138.Sx001.Sx094 and 2182[12]-138.SX001.Sx090) to the 218-11.30(HL) control plants, specific canola lines were identified which would contain fixed copies of the pDAB7305 T-strand integrants.

AnD9DS Genomic Integration Confirmation Via Southern Blot Analysis.

Southern blot analysis was used to establish the integration pattern of the inserted T-strand DNA fragment and identify canola lines which contained a full length AnD9DS gene expression cassette. Data were generated to demonstrate the integration and integrity of the transgene inserts within the canola genome. The detailed Southern blot analysis was conducted using a PCR amplified probe specific to the AnD9DS gene expression cassette. The hybridization of the probe with genomic DNA that had been digested with specific restriction enzymes identified genomic DNA fragments of specific molecular weights, the patterns of which were used to characterize the transgenic events for advancement to the next generation.

Tissue samples were collected in 2 mL conical tubes and lyophilized for 2 days. Tissue maceration was performed with a KLECKO™ tissue pulverizer and tungsten beads. Following tissue maceration, the genomic DNA was isolated using a CTAB isolation procedure. The genomic DNA was further purified using the Qiagen Genomic Tips™ kit. Genomic DNA was quantified by Quant-IT Pico Green DNA™ assay kit (Molecular Probes, Invitrogen, Carlsbad, Calif.). Quantified genomic DNA was adjusted to a consistent concentration.

For each sample, 4 μg of genomic DNA was thoroughly digested with the restriction enzyme BamHI (New England Biolabs, Beverley, Mass.). The digested DNA was concentrated by precipitation with Quick Precipitation Solution™ (Edge Biosystems, Gaithersburg, Md.) according to the manufacturer's suggested protocol. The genomic DNA was then resuspended in 25 μL of water at 65° C. for 1 hour. Resuspended samples were loaded onto a 0.8% agarose gel prepared in 1× TAE and electrophoresed overnight at 1.1 V/cm in 1× TAE buffer. The gel was sequentially subjected to denaturation (0.2 M NaOH/0.6 M NaCl) for 30 minutes, and neutralization (0.5 M Tris-HCl (pH 7.5)/1.5 M NaCl) for 30 minutes.

Transfer of DNA fragments to nylon membranes was performed by passively wicking 20× SSC solution overnight through the gel onto treated IMMOBILON™ NY+ transfer membrane (Millipore, Billerica, Mass.) by using a chromatography paper wick and paper towels. Following transfer, the membrane was briefly washed with 2× SSC, cross-linked with the STRATALINKER™ 1800 (Stratagene, LaJolla, Calif.), and vacuum baked at 80° C. for 3 hours.

Blots were incubated with pre-hybridization solution (Perfect Hyb plus, Sigma, St. Louis, Mo.) for 1 hour at 65° C. in glass roller bottles using a model 400 hybridization incubator (Robbins Scientific, Sunnyvale, Calif.). Probes were prepared from a PCR fragment containing the entire coding sequence. The PCR amplicon was purified using QIAEX II Gel Extraction Kit™ and labeled with DIG DNA Labeling Kit™ (Roche Applied BioSciencse, Indianapolis, Ind.). Blots were hybridized overnight at 65° C. with denatured probe added directly to hybridization buffer. Following hybridization, blots were sequentially washed at 65° C. with 0.1× SSC/0.1% SDS for 40 minutes. Finally, the blots were exposed to storage phosphor imaging screens and imaged using a Molecular Dynamics Storm 860™ imaging system.

The Southern blot analyses completed in this study were used to determine the copy number and confirm that selected events contained the AnD9DS gene expression cassette within the genome of canola. Table 5 provides the banding profile of multiple $T_2$ plants from selected lines based on the criteria defined above in Table 2. The control lines did not contain the selectable marker confirming the PCR data. Most of the lines selected from the three events show a homogeneous band pattern (number and size) except line from event 2182[12]-125.Sx001.Sx014. All three T2 lines from event 2182[12]-138.Sx001 display T2 populations with consistent banding pattern.

TABLE 5

Summary of Southern analysis completed on multiple T$_2$ canola lines from four transgenic events and the NEXERA 710 ™ canola control plants. The sizes of the observed bands for each sample were sized by comparison to a known standard run beside the samples on an agarose gel.

| Event- T$_2$ Line | Number of Plants | Band Numbers | Size Observed (Kb) |
| --- | --- | --- | --- |
| NEXERA 710 ™ | 2 | 0 | NA |
| 218-11.30(HL) | 2 | 4 | 5.8, 3.5, 1, 0.35* |
| 2182[12]-125.Sx001.Sx014 | 8 | 3 bands (2 plants) and 4 bands (6 plants) | 9.2, 4.4, 3.5, 2.6, 0.5 |
| 2182[12]-138.Sx001.Sx085 | 8 | 4 | 9.2, 5.8, 3.5, 0.7 |
| 2182[12]-138.Sx001.Sx090 | 8 | 4 | 9.2, 5.1, 2.5, 0.6 |
| 2182[12]-138.Sx001.Sx094 | 8 | 4 | 9.2, 5.1, 2.5, 0.6 |
| 2182[12]-156.Sx001.Sx049 | 8 | 2 | 4.5, 3.9 |

Example 6: T$_3$ Seed Yield of Selected Canola Lines

Selected plants from the T$_2$ canola lines were grown to maturity in the greenhouse. Seed was harvested from the plants. The seed was cleaned and the yield of seed per T$_2$ canola line was determined (Table 6). The yield of the seed from each line and compared to the yield of seed obtained from the untransformed control plants (Nexera™ 710GS) grown in the same conditions. Table 6 presents the yield results for the various plants which were obtained from each T$_2$ canola line. These results illustrate that the yield was variable for each plant and line tested. But that the average amounts of yield of the T$_2$ canola lines (2182[12]-125.Sx001.Sx014, 2182[12]-138.Sx001.Sx085, 2182[12]-138.Sx001.Sx090, 2182[12]-138.Sx001.Sx094, and 2182[12]-156.Sx001.Sx049) were relatively similar and did not significantly deviate from the control plants (Nexera™ 710G5 and 218-11.30(HL)).

TABLE 6

ANNOVA analysis of the seed yield, measured as total grams, from canola transgenic lines and the untransformed Nexera ™ 710GS control plants. Yield results are not significantly different ($p < 0.05$) for plants that are connected by the same letter in parenthesis.

| Event/Line | Plant Count | Ratio | Yield (g) |
| --- | --- | --- | --- |
| 218-11.30(HL) | 12 | 0.06186 | 5.7233333 (A, B) |
| 2182[12]-125.Sx001.Sx014 | 35 | 0.18041 | 5.9874286 (A, B) |
| 2182[12]-138.Sx001.Sx085 | 34 | 0.17526 | 6.8394118 (A) |
| 2182[12]-138.Sx001.Sx090 | 33 | 0.17010 | 6.4887879 (A, B) |
| 2182[12]-138.Sx001.Sx094 | 35 | 0.18041 | 5.0302857 (B) |
| 2182[12]-156.Sx001.Sx049 | 33 | 0.17010 | 6.3715152 (A, B) |
| Nexera ™ 710G5 | 12 | 0.06186 | 7.1666667 (A, B) |
| Total | 194 | 1.00000 | — |

Example 7: FAME Analysis of T$_3$ Canola Seeds Obtained from Transgenic pDAB7305 Canola Plants Both, single and bulked T$_3$ canola seeds were analyzed via the previously described FAME analysis method to characterize the fatty acid profile of the lines to identify specific lines which resulted in a reduction in total saturated fatty acids as compared to control plants. The sum of the total saturated fatty acids were quantitated and compared to positive control and negative control plants. The results confirmed that the total saturated fatty acid and saturated fatty acid (as determined from the sum of palmitic and stearic acid content) content of the single and bulked T$_3$ canola seed was reduced below 3.5% in the selected canola plant lines.

Surprisingly, two lines, 2182[12]-138.Sx001.Sx085 and 2182[12]-138.Sx001.Sx094, accumulated TSFA levels that averaged under 3.0%. Described for the first time are canola lines which are comprised of bulked seed that contains less than 3.0% saturated fatty acid. Table 7 and Table 8.

Figure 4:
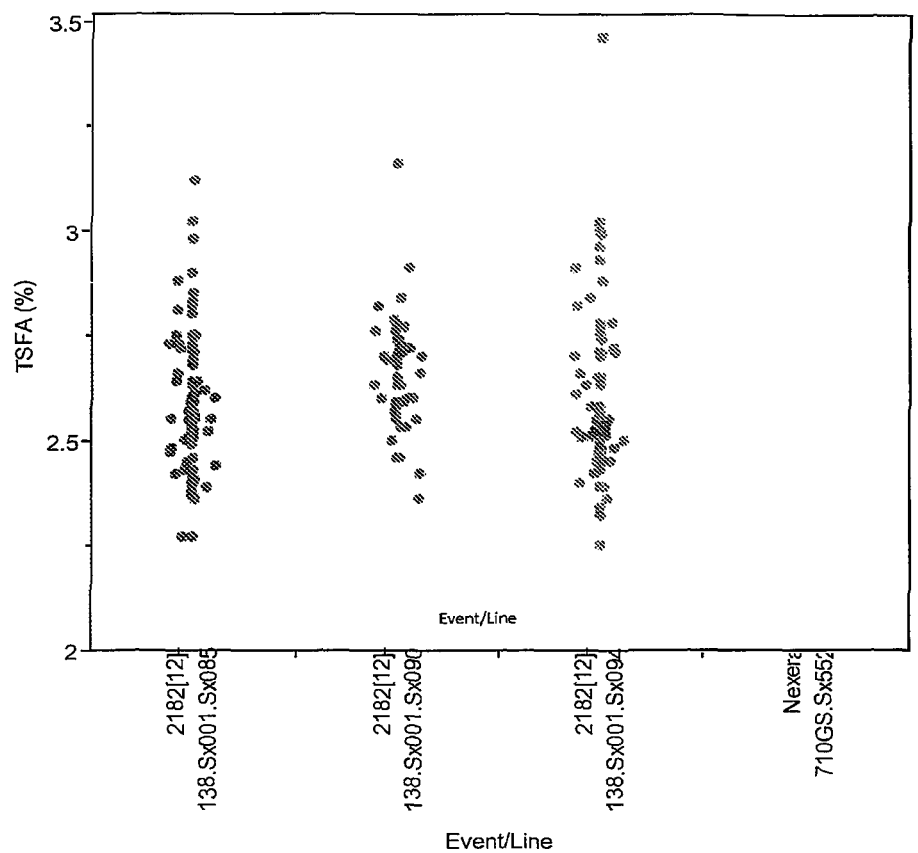
FIG. 4 illustrates the distribution of TSFA and saturated fatty acid percentage in canola single seed (wild type control plants are excluded so that the graphs depict the TSFA values of transgenic canola events).
Figure 4:
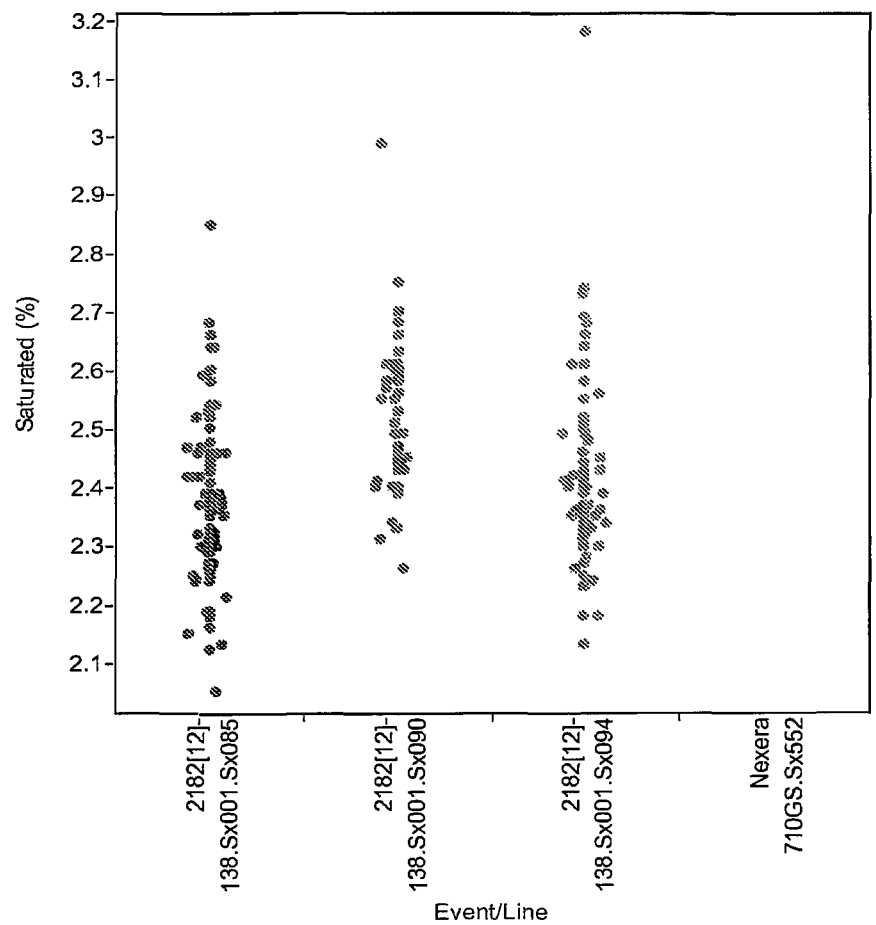

In addition, a sub-set of canola lines were used for seed FAME analysis to determine the lowest level of total saturated fatty acid and saturated fatty acid levels which could be obtained in a single canola seed. The single seed FAME analysis was completed on seeds obtained from the canola lines that were selected based on the lowest total saturated fatty acid of bulked seed and the high levels of plant yield. A total of 288 individual seeds were analyzed per line using the FAME method. The summary of the analysis is presented in Table 9. All single seeds from selected plants have a mean TSFA below 2.8%, which is significantly below the 3.5% TSFA level. The lowest TSFA level is 2.25% at the single seed canola level. This is significantly lower than the TSFA level of 5.11% which was obtained in the Nexera™ 710G5 control plants. Finally, the maximum TSFA percentage in the transgenic canola lines does not exceed 3.5% and the mean saturated level in single seed is 2.52% which is well below 3.5%. Table 9 and FIG. 4.

Table 7 shows the distribution of T$_2$ mature seed bulk FAMEs analysis for five populations of genetically homogenous canola lines as compared to the untransformed Nexera™ 710G5 controls and transformed 218-11.30(HL) positive control plants. The average of all the individual measurement (N) were determined to represent TSFA and saturated percentage for the population of canola plants. Canola lines, 2182[12]-138.Sx001.Sx085 and 2182[12]-138.Sx001.Sx094 are identified via bold print as these lines had an average TSFA percentage below 3.00 percent.

TABLE 7

| T$_2$ parent line | N | TSFA (%) | | | Saturated (%) | | |
| --- | --- | --- | --- | --- | --- | --- | --- |
|  |  | Mean | Min | Max | Mean | Min | Max |
| 218-11.30(HL) | 12 | 3.94 | 3.75 | 4.21 | 3.39 | 3.19 | 3.65 |
| 2182[12]-125.Sx001.Sx014 | 35 | 3.43 | 2.59 | 4.24 | 3.08 | 2.34 | 3.74 |
| 2182[12]-138.Sx001.Sx085 | 34 | 2.92 | 2.53 | 3.65 | 2.68 | 2.31 | 3.36 |
| 2182[12]-138.Sx001.Sx090 | 33 | 3.24 | 2.66 | 3.87 | 2.93 | 2.37 | 3.59 |
| 2182[12]-138.Sx001.Sx094 | 35 | 2.98 | 2.50 | 3.52 | 2.68 | 2.24 | 3.21 |
| 2182[12]-156.Sx001.Sx049 | 33 | 3.47 | 2.50 | 4.21 | 3.15 | 2.26 | 3.73 |
| Nexera 710G5 | 12 | 6.43 | 6.14 | 6.69 | 5.19 | 4.89 | 5.40 |

Table 8 shows the lowest T$_3$ mature seed bulk FAMEs and plant yield of single T$_2$ progeny plants obtained from event 2182[12]-138.Sx001 as compared to Nexera™ 710G5 control. The results displayed are for percentage of oil, percentage of TSFA, percentage of saturated fatty acids (as determined by summing the palmitic and stearic acid content), and seed yield.

TABLE 8

| Event/Line (T$_2$) | Oil (%) | TSFA (%) | Saturated (%) | TSFA Reduction (%) | Yield (g) |
|---|---|---|---|---|---|
| 2182[12]-138.Sx001.Sx094.Sx112 | 34.5 | 2.5 | 2.24 | 61.12 | 4.16 |
| 2182[12]-138.Sx001.Sx085.Sx070 | 38.7 | 2.53 | 2.31 | 60.65 | 6.05 |
| 2182[12]-138.Sx001.Sx085.Sx076 | 37.8 | 2.57 | 2.33 | 60.03 | 7.72 |
| 2182[12]-138.Sx001.Sx094.Sx122 | 39.3 | 2.65 | 2.41 | 58.79 | 5.73 |
| 2182[12]-138.Sx001.Sx090.Sx062 | 37.4 | 2.66 | 2.37 | 58.63 | 4.44 |
| Nexera 710GS.Sx552 | 43.7 | 6.28 | 5.15 | 2.33 | 6.97 |

Table 9 shows the distribution of T$_3$ single seed FAMEs analysis results from selected T$_2$ lines. The table shows the average (Mean), minimum (Min), and maximum (Max) TSFA and saturated fatty acid percentage, as compared to a Nexera™ 710G5 control canola plants that grown in the same condition. There was a reduction of total saturated fatty acids (TSFA) and saturated fatty acid level in T$_3$ seed of selected events as compared to a Nexera™ 710G5 control canola plants.

TABLE 9

| Events/Line | N | TSFA (%) Mean | TSFA (%) Min | TSFA (%) Max | Saturated (%) Mean | Saturated (%) Min | Saturated (%) Max |
|---|---|---|---|---|---|---|---|
| 2182[12]-138.Sx001.Sx085.Sx070 | 43 | 2.60 | 2.27 | 3.02 | 2.33 | 2.05 | 2.64 |
| 2182[12]-138.Sx001.Sx085.Sx076 | 48 | 2.57 | 2.27 | 3.12 | 2.40 | 2.16 | 2.85 |
| 2182[12]-138.Sx001.Sx090.Sx062 | 48 | 2.66 | 2.36 | 3.16 | 2.52 | 2.26 | 2.99 |
| 2182[12]-138.Sx001.Sx094.Sx112 | 48 | 2.51 | 2.25 | 2.78 | 2.38 | 2.13 | 2.61 |
| 2182[12]-138.Sx001.Sx094.Sx122 | 37 | 2.73 | 2.44 | 3.46 | 2.46 | 2.13 | 3.18 |
| Nexera 710GS.Sx552 | 48 | 6.34 | 5.71 | 7.52 | 5.11 | 4.73 | 5.90 |

What is claimed is:

1. A method for decreasing the amount of saturated fatty acids in oil from a plant, the method comprising:

transforming plant material with a nucleic acid molecule comprising a heterologous gene regulatory element operably linked to a polynucleotide encoding a delta-9 desaturase enzyme comprising an amino acid sequence that is at least 80% identical to SEQ ID NO:1, wherein the plant material also comprises an extraplastidial desaturase selected from the group consisting of LnD9DS desaturase, HzD9DS desaturase, and MgD9DS desaturase;

culturing the transformed plant material to obtain a plant; and extracting oil from the plant.

2. The method of claim 1, wherein the plant material is a seed.

3. The method of claim 1, wherein the plant is selected from a genus selected from the group consisting of *Arabidopsis, Borago, Canola, Ricinus, Theobroma, Zea, Gossypium, Crambe, Cuphea, Linum, Lesquerella, Limnanthes*, Linola, *Tropaeolum, Oenothera, Olea, Elaeis, Arachis*, rapeseed, *Carthamus, Glycine, Soja, Hehanthus, Nicotiana, Vernonia, Triticum, Hordeum, Oryza, Avena, Sorghum, Secale*, and the other members of the *Gramineae*.

* * * * *